US009487815B2

(12) United States Patent
Balss et al.

(10) Patent No.: US 9,487,815 B2
(45) Date of Patent: Nov. 8, 2016

(54) MEANS AND METHODS FOR THE DETERMINATION OF (D)-2-HYDROXYGLUTARATE (D2HG) OR (D)-2-HYDROXYADIPIC ACID

(71) Applicants: DKFZ Deutsches Krebsforschungszentrum, Heidelberg (DE); Ruprecht-Karls-Universität Heidelberg, Heidelberg (DE)

(72) Inventors: Jörg Balss, Dossenheim (DE); Stefan Pusch, Edingen-Neckarhausen (DE); Andreas Von Deimling, Schriesheim (DE); Wolfgang Buckel, Marburg (DE)

(73) Assignees: DKFZ Deutsches Krebsforschungszentrum, Heidelberg (DE); Ruprecht-Karls-Universität Heidelberg, Heidelberg (DE)

( * ) Notice: Subject to any disclaimer, the term of this patent is extended or adjusted under 35 U.S.C. 154(b) by 0 days.

(21) Appl. No.: 14/381,835

(22) PCT Filed: Mar. 1, 2013

(86) PCT No.: PCT/EP2013/054160
§ 371 (c)(1),
(2) Date: Aug. 28, 2014

(87) PCT Pub. No.: WO2013/127997
PCT Pub. Date: Sep. 6, 2013

(65) Prior Publication Data
US 2015/0044716 A1 Feb. 12, 2015

(30) Foreign Application Priority Data
Mar. 1, 2012 (EP) .................................... 12157663

(51) Int. Cl.
C12Q 1/32 (2006.01)
G01N 33/574 (2006.01)

(52) U.S. Cl.
CPC ........... *C12Q 1/32* (2013.01); *G01N 33/57407* (2013.01); *C12Q 2326/00* (2013.01); *G01N 2333/904* (2013.01); *G01N 2458/15* (2013.01); *G01N 2800/046* (2013.01); *G01N 2800/22* (2013.01); *G01N 2800/28* (2013.01)

(58) Field of Classification Search
CPC ................. C12Q 1/32; C12Q 2326/00; G01N 2333/904; G01N 2458/15; G01N 2800/046; G01N 2800/22; G01N 2800/28; G01N 33/57407; C12N 9/2437; C12Y 302/01004; C12Y 302/01006; C12Y 302/01015; C12Y 302/01039; C12Y 302/01; A61K 2300/00; A61K 31/122; A61K 31/00; A61K 31/05; A61K 31/16; A61K 31/166; A61K 36/13; A61K 31/145; A61K 31/52; A61K 31/7088; A61K 45/06; A61K 36/74; A61K 2039/6025; A61K 2039/70; A61K 31/04
See application file for complete search history.

(56) References Cited

PUBLICATIONS

International Preliminary Report on Patentability issued in related International Patent Application No. PCT/EP2013/054160, dated Sep. 12, 2014.
Abbas et al., "Acquired mutations in the genes encoding IDH1 and IDH2 both are recurrent aberrations in acute myeloid leukemia: prevalence and prognostic value," Blood, 116: pp. 2122-2126 (2010).
Achouri et al., "Identification of a dehydrogenase acting on D-2-hydroxyglutarate," Biochem. J. 381: pp. 35-42 (2004).
Alizadeh et al., "Evaluation and Management of Angioimmunoblastic T-cell Lymphoma: A Review of Current Approaches and Future Strategies," Clin. Advances in Hematol. and Oncol. 6(12): pp. 899-909 (2008).
Altman, "Tetrazolium Salts and Formazans," Prog. Histochem. Cytochem. 9: pp. 1-56 (1976).
Amary et al., "IDH1 and IDH2 mutations are frequent events in central chondrosarcoma and central and periosteal chondromas but not in other mesenchymal tumours," J. Pathol., 224: pp. 334-343 (2011).
Balss et al., "Analysis of the IDH1 codon 132 mutation in brain tumors," Acta Neuropathol., 116: 597-602 (2008).

(Continued)

Primary Examiner — Debbie K Ware
(74) Attorney, Agent, or Firm — Foley & Lardner LLP

(57) ABSTRACT

The present invention relates to a method for detecting (D)-2-hydroxyglutarate or (D)-2-hydroxyadipic acid in a sample, the method comprising the steps of: a) contacting a sample with a reagent mixture, wherein said reagent mixture comprises: (i) a solvent, (ii) a dye having an oxidized state and a reduced state, wherein the reduced state can be distinguished from the oxidized state and wherein the dye is initially present in the oxidized state, (iii) an electron transfer agent, (iv) a (D)-2-hydroxyglutarate dehydrogenase enzyme, and (v) a cofactor; and b) detecting (D)-2-hydroxyglutarate or (D)-2-hydroxyadipic acid by measuring the production of the reduced state of the dye. The invention further pertains to a method for diagnosing and/or monitoring a (D)-2-hydroxy-glutarate-associated disease in a subject. Encompassed by the invention is also a method for diagnosing a mutation in an isocitrate dehydrogenase (IDH) gene or in a (D)-2-hydroxyglutarate (D2HG) dehydrogenase enzyme gene in a subject. In addition, the invention provides for a kit comprising (i) a solvent, (ii) a dye having an oxidized state and a reduced state, wherein the reduced state can be distinguished from the oxidized state and wherein the dye is initially present in the oxidized state, (iii) an electron transfer agent, (iv) a (D)-2-hydroxyglutarate dehydrogenase enzyme, and (v) a cofactor.

15 Claims, 16 Drawing Sheets

(56) References Cited

PUBLICATIONS

Figure 1:
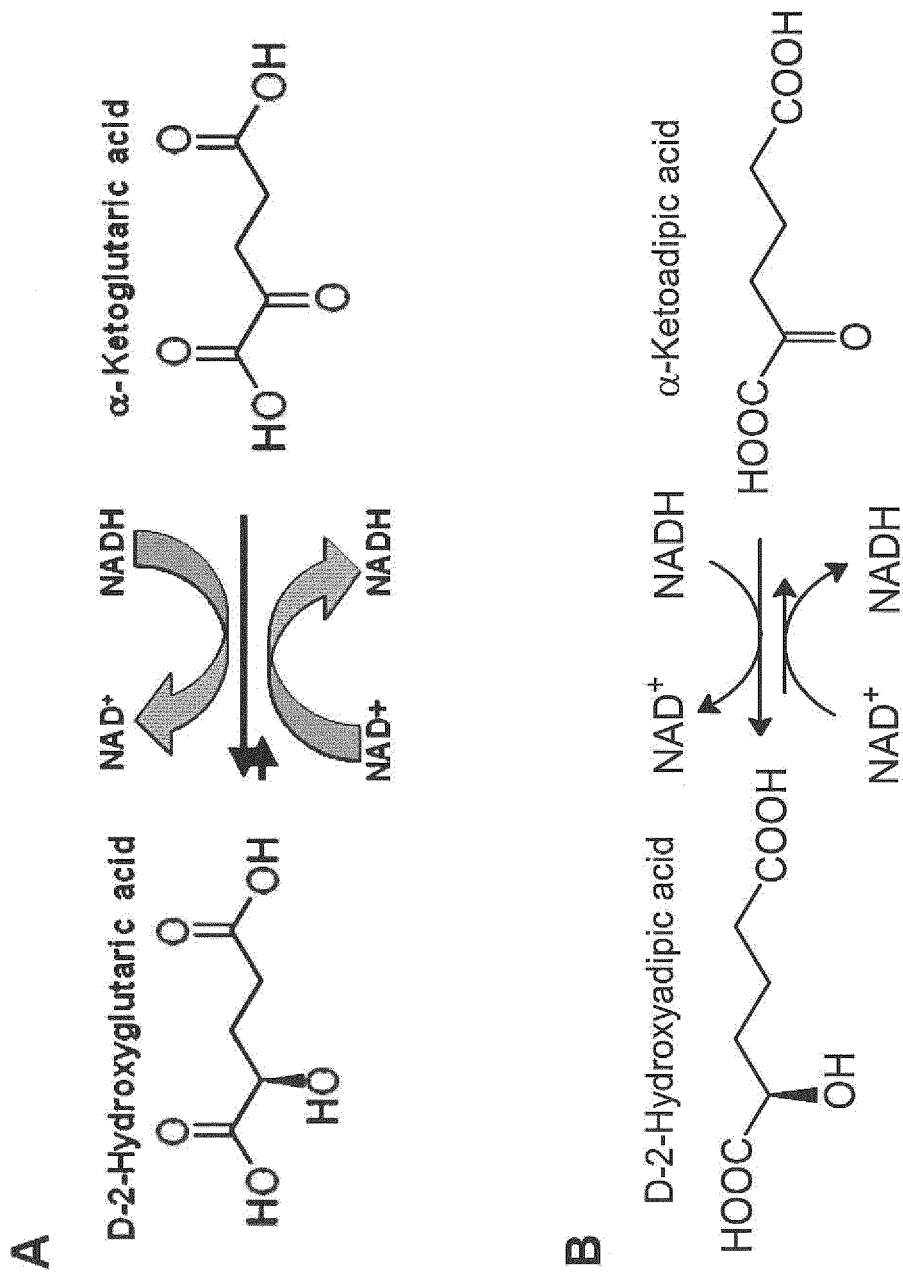
Figure 1:
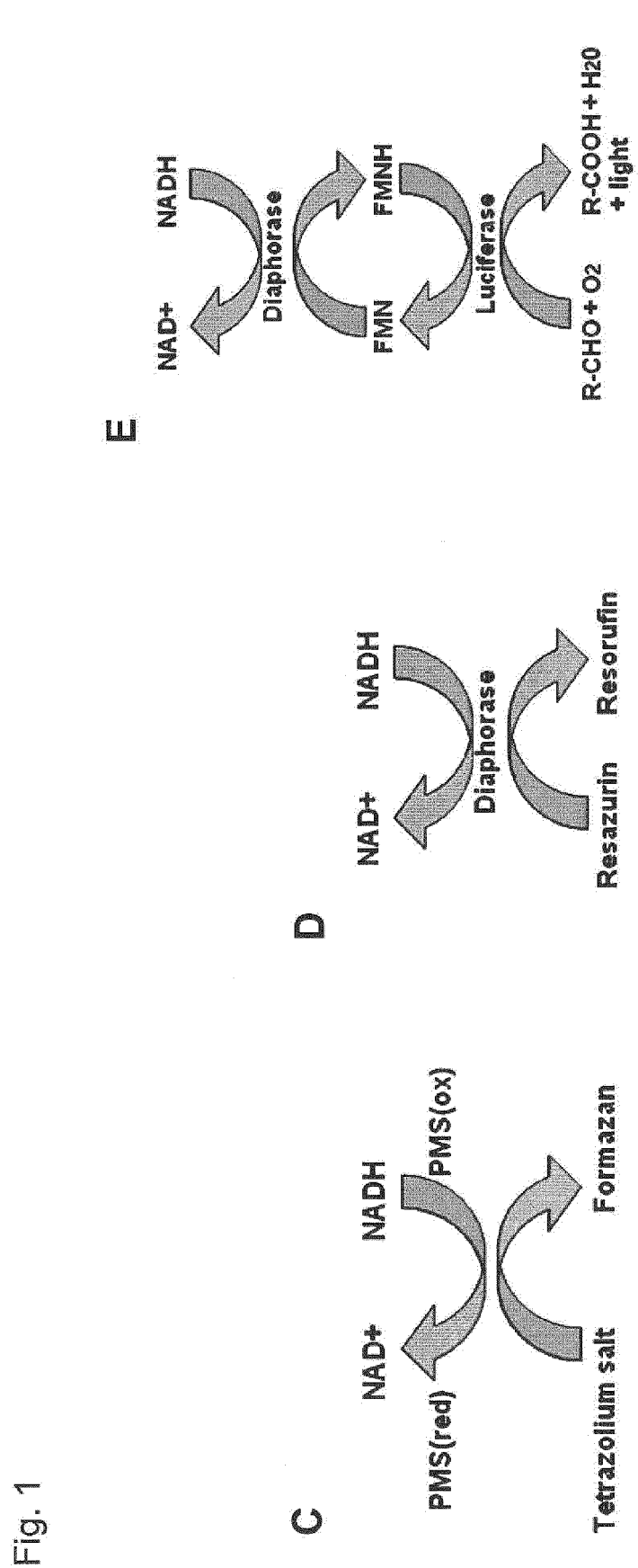

Berridge et al., "Tetrazolium dyes as tools in cell biology: New insights into their cellular reduction," Biotechnology Annual Review 11: 127-152 (2005).

Bijarnia et al., "Glutaric aciduria type I: outcome following detection by newborn screening," J. Inherit.Metab. Dis. 31: 503-507 (2008).

Bjugstad et al., "Age at symptom onset predicts severity of motor impairment and clinical outcome of glutaric acidemia type 1," J. Pediatr. 137: 681-686 (2000).

Boneh et al., "Newborn screening for glutaric aciduria type I in Victoria: Treatment and outcome," Mol. Genet. Metab. 94: 287-291 (2008).

Borger et al., "Frequent Mutation of Isocitrate Dehydrogenase (IDH)1 and IDH2 in Cholangiocarcinoma Identified Through Broad-Based Tumor Genotyping," The Oncologist 17: 72-79 (2012).

Buckel, "The Reversible Dehydration of (R)-2-Hydroxyglutarate to (E)-Glutaconate," Eur. J. Biochem., 106: 439-447 (1980).

Busquets et al., "Glutaryl-CoA Dehydrogenase Deficiency in Spain: Evidence of Two Groups of Patients, Genetically, and Biochemically Distinct," Pediatr. Res. 48: 315-322 (2000).

Buttke et al., "Use of an aqueous soluble tetrazolium/formazan assay to measure viability and proliferation of lymphokine-dependent cell lines," J. Immunol. Methods, 157: 233-240 (1993).

Cairns et al., "IDH2 mutations are frequent in angioimmunoblastic T-cell lymphoma," Blood, pp. 1901-1903 (2012).

Capper et al., "Monoclonal antibody specific for IDH1 R132H Mutation," Acta Neuropathol., 218: 599-601 (2009).

Capper et al., "2-Hydroxyglutarate concentration in serum from patients with gliomas does not correlate with IDH1/2 mutation status or tumor size," International Journal of Cancer, pp. 766-768 (2011).

Chou et al., "Persistence of mutant dehydrogenase in patients with acute myeloid leukemia in remission," Leukemia, pp. 527-562 (2011).

Claus et al., "Survival Rates and Patterns of Care for Patients Diagnosed with Supratentorial Low-Grade Bliomas," Cancer, pp. 1358-1363 (2006).

Damm et al., "Prevalance and prognostic value of IDH1 and IDH2 mutations in childhood AML: a study of the AML-BFM and DCOG study groups," Leukemia, pp. 1704-1710 (2011).

Dang et al., "Cancer-associated IDH1 mutations produce 2-hydroxyglutarate," Nature, vol. 462, pp. 739-744 (2009).

Döhner et al., "Impact of Genetic Features on Treatment Decisions in AML," ASH Education Program Book, pp. 36-42 (2011).

Dunigan et al., "Aqueous Soluble Tetrazolium/Formazan MTS as an Indicator of NADH- and NADPH-and NADPH-Dependent Dehydrogenase Activity," BioTechniques, 19, pp. 640-649 (1995).

Engqvist et al., "Two D-2-Hydroxy-acid dejydrogenases in Arabidopsis thaliana with Catalytic Capacities to Participate in the Last Reactions of the Methylglyoxal and B-Oxidation Pathways," J. Biol. Chem., vol. 284, No. 37, pp. 25026-25037 (2009).

Ferroli et al., "From standard treatment of Personalized Medicine: Role of IDH1 Mutations in Low-Grade Bioma Evolution and Treatment," World Neurosurg 73: pp. 234-236 (2010).

Geisbrecht et al., "The Human PICD Gene Encodes a Cytoplasmic and Peroxisomal NADP+-dependent Isocitrate Dehydrogenase," J. Biol. Chem., 274: pp. 30527-30533 (1999).

Georgiou et al., "Development of acute myeloid leukemia with NPM1 mutation, in Ph-negative clone, during treatment of CML with imatinib," 2011, Leukemia at 824-826 (2011).

Goodman et al., "Glutaric Aciduria; A "New" Disorder of Amino Acid Metabolism," Biochem. Med. 12: 12-21 (1975).

Greenberg et al., Outcome of the First 3-Years of a DNA-Based Neonatal Screening Program for Glutric Acidemia Type 1 in Manitoba and Northwestern Ontario, Canada, Mol. Gen. Metab. 75: pp. 70-78 (2002).

Hartmann et al., Molecular Markers in Low-Grade Bliomas: Predictive or Prognostic?, Clinical Cancer Research 17: pp. 4588-4599 (2011).

Hartmann et al., "Type and frequence of IDH1 and IDH2 mutations are related to astrocytic and oligodendroglial differentiation and age: a study of 1,010 diffuse gliomas," Acta Neuropathol., 118: 469-474 (2009).

Hays et al., "Dietary Glutamate Is Almost Entirely Removed in Its First Pass Through the Splanchnic Bed in Premature Infants," Pediatr. Res. 62: 353-362 (2007).

Heringer et al., "Use of Guidelines Improes the Neurological Outcome in Glutaric Aciduria Type 1," Ann. Neurol. 68: 743-752 (2010).

Hoffmann et al., "Glutaryl-Coenzyme A Dehydrogenase Deficiency: A Distinct Encephalopathy," Pediatrics 88: 1194-1203 (1991).

Hoffmann et al., "Clinical Couse, Early Diagnosis, Treatment, and Prevention of Disease in Glutaryl-CoA Dehydrogenase Deficiency," Neuropediatrics 27: 115-123 (1996).

Kölker et al., Guideline for the diagnosis and management of glutaryl-CoA dehydrogenase deficiency (glutaric aciduria type I), J. Inherit. Metab. Dis. 30: pp. 5-22 (2007).

Kranendijk et al., "IDH2 Mutations in Patients with D-2-Hydroxyglutaric Aciduria," Science 330: p. 336 (2010).

Kranendijk et al., "Development and implementation of a novel assay for L-2-hydroxyglutarate dehydrogenase (I-2-HGDH) in cell lysates: L-2-HGDH deficiency in 15 patients with L-2-hydroxyglutaric aciduria," Journal of Inherited Metabolic Disease, 32, pp. 713-719 (2009).

Kyllerman et al., "Dystonia and dyskinesia in Glutaric Aciduria Type I: Clinical Heterogeneity and Therapeutic Considerations," Mov. Disord. 9: pp. 22-30 (2004).

Latini et al., "Mitochondrial energy metabolism is markedly impared by D-2-hydroxyglutaric acid in rat tissues," Molecular Genetics and Metabolism, 86, pp. 188-199 (2005).

Lin et al, "Nontargeted Urinary Metabolite Profiling of a Mouse Model of Crohn's Disease," Journal of Proteome Research, 8, pp. 2045-2057 (2009).

Lindner et al., "Neonatal Screening for Glutaric Aciduria Type I: Strategies to proceed," J. Inherit. Metab. Dis. 29: 378-382 (2006).

Mardis et al., "Recurring Mutations Found by Sequencing an Acute Myeloid Leukemia Genome," New England Journal of Medicine, 361: 1058-1066 (2009).

Marshall et al., "A Critical Assessment of the Use of Miroculture Tetrazolium Asays to Measure Cell Growth and Function," Growth Regulation 5: pp. 69-84 (1999).

Martins et al., "Structural basis for stereo-specific catalysis in NAD+-dependent (R)-2-hydroxyglutarate dehydrogenase from Acidaminococcus fermentans," *FEBS J.* Jan. 2005; 272(1): 269-81 (2005).

Mukasa et al., "Significance of IDH mutations varies with Tumor Histology, Grade, and Genetics in Japanese Glioma Patients," Cancer Science, vol. 103, No. 3, pp. 587-592 (2012).

Murugan et al., "Identification and functional characterization of isocitrate dehydrogenase 1 (IDH1) Mutations in Thyroid Cancer," BBRC 393: 555-559 (2010).

Naughten et al., "Glutaric aciduria type I: Outcome in the Republic of Ireland," J. Inherit. Metab. Dis. 27: 917-920 (2004).

Parsons et al., "An Integrated Genomic Analysis of Human Glioblastoma Multiforme," Science 321, 1807-1812 (2008).

Parthasarathy et al., "Substrate Specificity of 2-Hydroxyglutaryl-CoA Dehydratase from Clostridium Symbiosum: Toward a Bio-Based production of Adipic Acid," Biochemistry, 50(17): 3540-50 (2001).

Parthasarathy et al., "Correction to Substrate Specificity of 2-Hydroxyglutaryl-CoA Dehydratase from Clostridium symbiosum: Toward a Bio-Based Production of Adipic Acid," Biochemistry, 50(20): p. 4392 (2011).

Paschka et al., "IDH1 and IDH2 Mutations are frequent Genetic alterations in Acute Myeloid Leukemia and Confer Adverse prognosis in Cytogenetically Normal Acute Myeloid Leukemia with NPM1 Mutation without FLT3 Internal Tandem Duplication," J. Clin. Oncol., 28: 3636-3643 (2010).

(56) References Cited

OTHER PUBLICATIONS

Pei et al., "Acyl-CoA Synthetase VL3 Knockdown Inhibits Human Glioma Cell Proliferation and Tumorigenicity," Cancer Res., vol. 69, No. 24, pp. 9175-9182 (plus Supplemental Figures and Figure Legends), (2009).
Rakheja et al., "High incidence of IDH mutations in acute myeloid leukaemia with cuplike nuclei," British Journal of Haematology 155: pp. 125-128 (2011).
Ravandi et al., "Prognostic Significance of Alterations in IDH Enzyme Isoforms in Patients with AML Treated with High-dose Cytarabine and Idarubicin," Cancer, pp. 2665-2673 (2012).
Reitman et al., "Enzyme redesign guided by cancer-derived IDH1 mutations," Nature Chemical Biology 8: 887-889 (2012).
Sahm et al., "Detection of 2-Hydroxyglutarate in formalin-fixed Paraffin-embedded glioma specimens by Gas Chromatography/Mass Spectrometry," Brain Pathology, pp. 26-31 (2010).
Sanai, et al., "Low-grade gliomas in adults," Journal of Neurosurgery 115: 948-965 (2011).
Schnittger et al., "IDH1 mutations are detected in 6.6% of 1414 AML patients and are associated with intermediate risk karyotype and unfavourable prognosis in adults younger than 60 years and unmutated NPM1 status," Blood, 116: 5486-5496 (2010).
Scudiero et al., "Evaluation of a Soluble Tetrazolium/Formazan Assay for Cell Growth and Drug Sensitivity in Culture Using Human and Other Tumor Cell Lines," Cancer Res. 48: 4827-4833 (1988).
Sellner et al., "Increased levels of 2-hydroxyglutarate in AML patients with IDH1-R132H and IDH2-R140Q Mutations," Eur. J. Haematol., 85: 457-459 (2010).
Sherman, "Low-Grade Gliomas", Primary Central Nervous System Tumors, pp. 173-194 (2011).
Sjöblom et al., "The Consensus Coding Sequences of Human Breast and Colorectal Cancers," Science 314: 268-274 (2006).
Soffietti et al., "Guidelines on management of low-grade gliomas: report of an EFNS-EANO Task Force," European Journal of Neurology 17: 1124-1133 (2010).
Soundar et al., "Identification by Mutagenesis of Arginines in the Substraet Binding Site of the Porcine NADP-dependent Isocitrate Dehydrogenase," J. Biol. Chem., 275: 5606-5612 (2000).
Sponholz et al., "Enzymatische Bestimmung von (R)-2-Hydroxyglutarsaure in Mosten, Weinen and anderen Garungsgetranken," Zeitschrift für Lebensmittel-Untersuchung und -Forschung, 172: 264-268 (1981).
Strauss et al., "Type I Glutaric Aciduria, Part 1: Natural History of 77 Patients," Am. J. Med. Genet. 121C: 38-52 (2003).
Strauss et al., "Multimodal Imaging of Striatal Degeneration in Amish patients with glutaryl-CoA dehydrogenase Deficiency," Brain 130: 1905-1920 (2007).
Struys et al., "D-2-Hydroxyglutaric aciduria in three patients with proven SSADH deficiency: Genetic coincidence or a related biochemical epiphenomenon?", Molecular Genetics and Metabolism 88(1): 53-57 (2006).
Struys et al., "Measurement of Urinary D- and L-2-Hydroxyglutarate Enantiomers by Stable-Isotope-Dilution Liquid Chromatography-Tandem Mass Spectrometry after Derivatization with Diacetyl-L-Tartaric Anhydride," Clinical Chemistry, 50, pp. 1391-1395 (2004).
Thon et al., "IDH1 Mutations in Grade II Astrocytomas are Associated with Unfavorable Progression-Free Survival and Prolonged Postrecurrence Survival," Cancer 118: 452-460 (2012).
van den Bent et al., "IDH1 and IDH2 Mutations are Prognostic but not Predictive for Outcome in Anaplstic Oligodendroglial Tumors: A Report of the European Organization for Research and Treatment of Cancer brain Tumor Group," Clinical Cancer Research 16: 1597-1604 (2010).
Vaughan et al., "Determination of nanomolar levels of formate in natural waters based on a luminescence enzymatic assay," Analytica Chimica Acta 231: 299-303 (1990).
Ward et al., "Identification of additional IDH mutations associated with oncometabolite R(−)-2-hydroxyglutarate production," Oncogene, vol. 31, pp. 2491-2498 (2011).
Weller, "Novel diagnostic and therapeutic approaches to malignant glioma," Swiss Med Wkly 141 pp. 13210-16 (2011).
Wienhausen et al., "Bioluminescent Assays of Pocomole Levels of Various Metabolites Using Immobilized Enzymes," Analytical Biochemistry 127: 380-388 (1982).
Wickenhagen et al., "Measurement of D-2-hydroxyglutarate dehydrogenase activity in cell homogenates derived from D-2-hydroxyglutaric aciduria patients," Journal of Inherited Metabolic Disease, 32(2), pp. 264-268 (2009).
Zhao et al., "Glioma-Derived Mutations in IDH1 Dominantly Inhibit IDH1 Catalytic Activity and Induce HIF-1α," Science, 324: 261-265 (2009).
International Search Report issued in related International Patent Application No. PCT/EP2013/054160, dated Jun. 17, 2013.

Fig. 3

| | Stock concentration | End concentration in assay | | Volumes [µl] | |
|---|---|---|---|---|---|
| | | PMS/XTT | Diaphorase/ resazurin | PMS/XTT | Diaphorase/ resazurin |
| Tris buffer pH 8.0 | 1 M | 100 mM | 100 mM | 10 | 10 |
| NAD⁺ | 10 mM | 100 µM | 100 µM | 1 | 1 |
| PMS | 82.5 µM | 8.25 mM | - | 10 | - |
| XTT | 1.5 mM | 150 µM | - | 10 | - |
| Diaphorase | 0.01 U/µl | - | 0.1 U/100µl | - | 1 |
| Resazurin | 125 nM | - | 12.5 nM | - | 10 |
| D2HGDH | 0.1 µg/µl | 0.1 µg | 0.1 µg/100 µl | 1 | 1 |
| Water | - | - | - | 43 | 52 |
| Sample | - | - | - | 25 | 25 |

Fig. 4

| pmol/µl | nmol/ml | µM | in 25 µl sample volume | |
|---|---|---|---|---|
| | | | pmol | |
| | | 0 | 0 | |
| | | 5 | 125 | |
| | | 10 | 250 | |
| | | 25 | 625 | |
| | | 50 | 1250 | |
| | | 100 | 2500 | |
| | | 250 | 6250 | |
| | | 500 | 12500 | |

Fig. 10

| | Name | Organism | Protein length | Accession number |
|---|---|---|---|---|
| 1 | D-2-hydroxyglutarate dehydrogenase | Arabidopsis thaliana | 559 aa protein | AEE86652.1 GI:332661252 |
| 2 | D-2-hydroxyglutarate dehydrogenase | Arabidopsis thaliana | 559 aa protein | AEE86651.1 GI:332661251 |
| 3 | D-2-hydroxyglutarate dehydrogenase | Taylorella equigenitalis MCE9 | 474 aa protein | YP_004130018.1 GI:319779105 |
| 4 | D-2-hydroxyglutarate dehydrogenase | Taylorella equigenitalis MCE9 | 449 aa protein | YP_004129640.1 GI:319778727 |
| 5 | D-2-hydroxyglutarate dehydrogenase | Oligotropha carboxidovorans OM5 | 470 aa protein | ACI94033.1 GI:209874237 |
| 6 | D-2-hydroxyglutarate dehydrogenase | Taylorella asinigenitalis MCE3 | 455 aa protein | AEP37253.1 GI:347974718 |
| 7 | D-2-hydroxyglutarate dehydrogenase | Taylorella asinigenitalis MCE3 | 474 aa protein | AEP36112.1 GI:347973577 |
| 8 | D-2-hydroxyglutarate dehydrogenase | Rhodobacter capsulatus SB 1003 | 469 aa protein | ADE86817.1 GI:294477429 |
| 9 | D-2-hydroxyglutarate dehydrogenase | Rhodobacter capsulatus SB 1003 | 458 aa protein | ADE84932.1 GI:294475544 |
| 10 | D-2-hydroxyglutarate dehydrogenase | Mycobacterium smegmatis str. MC2 155 | 451 aa protein | ABK75290.1 GI:118174394 |
| 11 | D-2-hydroxyglutarate dehydrogenase | Oceanicola sp. S124 | 473 aa protein | ZP_09514146.1 GI:372278110 |
| 12 | D-2-hydroxyglutarate dehydrogenase | Advenella kashmirensis WT001 | 477 aa protein | ZP_09480509.1 GI:371504788 |
| 13 | D-2-hydroxyglutarate dehydrogenase | Mustela putorius furo | 477 aa protein | AER96945.1 GI:355682357 |
| 14 | D-2-hydroxyglutarate dehydrogenase | Pelagibacterium halotolerans B2 | 480 aa protein | AEQ53776.1 GI:351595439 |
| 15 | D-2-hydroxyglutarate dehydrogenase | Pelagibacterium halotolerans B2 | 470 aa protein | AEQ50623.1 GI:351592286 |
| 16 | D-2-hydroxyglutarate dehydrogenase | Pseudomonas fluorescens F113 | 477 aa protein | AEV65873.1 GI:359763794 |
| 17 | D-2-hydroxyglutarate dehydrogenase | Pseudomonas fluorescens F113 | 472 aa protein | AEV60287.1 GI:359758208 |
| 18 | D-2-hydroxyglutarate dehydrogenase | Burkholderia cenocepacia H111 | 476 aa protein | CCE49315.1 GI:358073259 |
| 19 | D-2-hydroxyglutarate dehydrogenase | Burkholderia cenocepacia H111 | 474 aa protein | CCE51634.1 GI:358070865 |
| 20 | D-2-hydroxyglutarate dehydrogenase | Medicago truncatula | 724 aa protein | XP_003612098.1 GI:357483623 |
| 21 | D-2-hydroxyglutarate dehydrogenase | Medicago truncatula | 724 aa protein | AES95056.1 GI:355513433 |
| 22 | D-2-hydroxyglutarate dehydrogenase | Taylorella equigenitalis MCE9 | 474 aa protein | ADU91875.1 GI:317109129 |
| 23 | D-2-hydroxyglutarate dehydrogenase | Taylorella equigenitalis MCE9 | 449 aa protein | ADU91497.1 GI:317108751 |
| 24 | D-2-hydroxyglutarate dehydrogenase | Rhodobacter capsulatus SB 1003 | 469 aa protein | YP_003579224.1 GI:294678609 |
| 25 | D-2-hydroxyglutarate dehydrogenase | Rhodobacter capsulatus SB 1003 | 458 aa protein | YP_003577339.1 GI:294676724 |

Fig. 10 (Continued)

| | Name | Organism | Protein length | Accession number |
|---|---|---|---|---|
| 26 | D-2-hydroxyglutarate dehydrogenase | Candidatus Burkholderia kirkii UZHbot1 | 484 aa protein | ZP_08913802.1 GI:350544153 |
| 27 | D-2-hydroxyglutarate dehydrogenase | Candidatus Burkholderia kirkii UZHbot1 | 484 aa protein | CCD36612.1 GI:350528066 |
| 28 | D-2-hydroxyglutarate dehydrogenase | Ascaris suum | 496 aa protein | ADY45404.1 GI:324513120 |
| 29 | D-2-hydroxyglutarate dehydrogenase | Ascaris suum | 496 aa protein | ADY45038.1 GI:324512144 |
| 30 | D-2-hydroxyglutarate dehydrogenase | Ascaris suum | 496 aa protein | ADY44867.1 GI:324511708 |
| 31 | D-2-hydroxyglutarate dehydrogenase | Silicibacter lacuscaerulensis ITI-1157 | 482 aa protein | EEX08148.1 GI:260414889 |
| 32 | D-2-hydroxyglutarate dehydrogenase | gamma proteobacterium NOR51-B | 458 aa protein | EED35311.1 GI:219678962 |
| 33 | D-2-hydroxyglutarate dehydrogenase | Roseobacter sp. GAI101 | 473 aa protein | EEB85861.1 GI:214045223 |
| 34 | D-2-hydroxyglutarate dehydrogenase | Bradyrhizobiaceae bacterium SG-6C | 475 aa protein | ZP_08628720.1 GI:338973356 |
| 35 | D-2-hydroxyglutarate dehydrogenase | Bradyrhizobiaceae bacterium SG-6C | 475 aa protein | EGP08525.1 GI:338233399 |
| 36 | D-2-hydroxyglutarate dehydrogenase | Rhodococcus erythropolis SK121 | 468 aa protein | ZP_04385524.1 GI:229491703 |
| 37 | D-2-hydroxyglutarate dehydrogenase | gamma proteobacterium NOR5-3 | 466 aa protein | EED33412.1 GI:219677047 |
| 38 | D-2-hydroxyglutarate dehydrogenase | Arabidopsis thaliana | 559 aa protein | NP_974692.1 GI:42573191 |
| 39 | D-2-hydroxyglutarate dehydrogenase | Arabidopsis thaliana | 559 aa protein | NP_568003.2 GI:42567457 |
| 40 | D-2-hydroxyglutarate dehydrogenase | Ahrensia sp. R2A130 | 473 aa protein | ZP_07375397.1 GI:304393469 |
| 41 | D-2-hydroxyglutarate dehydrogenase | Salpingoeca sp. ATCC 50818 | 515 aa protein | EGD78013.1 GI:326432443 |
| 42 | D-2-hydroxyglutarate dehydrogenase | Capsaspora owczarzaki ATCC 30864 | 526 aa protein | EFW42114.1 GI:320165215 |
| 43 | D-2-hydroxyglutarate dehydrogenase | Daphnia pulex | 506 aa protein | ACT20727.1 GI:251825187 |
| 44 | D-2-hydroxyglutarate dehydrogenase | Silicibacter lacuscaerulensis ITI-1157 | 482 aa protein | ZP_05785032.1 GI:260431061 |
| 45 | D-2-hydroxyglutarate dehydrogenase | gamma proteobacterium NOR5-3 | 466 aa protein | ZP_05126865.1 GI:254514804 |
| 46 | D-2-hydroxyglutarate dehydrogenase | Roseobacter sp. GAI101 | 473 aa protein | ZP_05101559.1 GI:254488354 |
| 47 | D-2-hydroxyglutarate dehydrogenase | gamma proteobacterium NOR51-B | 458 aa protein | ZP_04957727.1 GI:254282759 |
| 48 | D-2-hydroxyglutarate dehydrogenase | Ahrensia sp. R2A130 | 473 aa protein | EFL88848.1 GI:303294476 |
| 49 | D-2-hydroxyglutarate dehydrogenase | Mus musculus | 535 aa protein | AAI17795.1 GI:109734866 |
| 51 | D-2-hydroxyglutarate dehydrogenase | Bos taurus | 544 aa protein | ABF57376.1 GI:95768700 |

Fig. 10 (Continued)

| | Name | Organism | Protein length | Accession number |
|---|---|---|---|---|
| 52 | D-2-hydroxyglutarate dehydrogenase | Rhodococcus erythropolis SK121 | 468 aa protein | EEN87184.1 GI:229321384 |
| 53 | D-2-hydroxyglutarate dehydrogenase | Homo sapiens | 521 aa protein | AAH36604.2 GI:34192567 |
| 54 | D-2-hydroxyglutarate dehydrogenase, mitochondrial precursor | Homo sapiens | 521 aa protein | NP_689996.4 GI:119964728 |
| 55 | D-2-hydroxyglutarate dehydrogenase, mitochondrial precursor | Bos taurus | 544 aa protein | NP_001069446.1 GI:115496047 |
| 57 | D-2-hydroxyglutarate dehydrogenase, mitochondrial precursor | Mus musculus | 535 aa protein | NP_849213.2 GI:170014723 |
| 58 | D-2-hydroxyglutarate dehydrogenase, mitochondrial | Rattus norvegicus | 528 aa protein | NP_001100396.1 GI:157818371 |
| 59 | D-2-hydroxyglutarate dehydrogenase, mitochondrial precursor | Danio rerio | 533 aa protein | NP_001074066.1 GI:123705184 |

Fig. 11

|  | Stock conzentration | End conzentration in the assay |
|---|---|---|
| Tris buffer pH 8.0 | 1 M | 100 mM |
| NAD+ | 10 mM | 100 µM |
| PMS | 82,5 µM | - |
| XTT | 1,5 mM | - |
| Diaphorase | 0,1 U/µl | 0,1 U/100 µl |
| Resazurin | 125 nM | 12,5 nM |
| D2HGDH | 0,1 µg/µl | 4 µg/100 µl |
| Water | - | - |
| Sample | - | - |

MEANS AND METHODS FOR THE DETERMINATION OF (D)-2-HYDROXYGLUTARATE (D2HG) OR (D)-2-HYDROXYADIPIC ACID

The present invention relates to a method for detecting (D)-2-hydroxyglutarate or (D)-2-hydroxyadipic acid in a sample, the method comprising the steps of: a) contacting a sample with a reagent mixture, wherein said reagent mixture comprises: (i) a solvent, (ii) a dye having an oxidized state and a reduced state, wherein the reduced state can be distinguished from the oxidized state and wherein the dye is initially present in the oxidized state, (iii) an electron transfer agent, (iv) a (D)-2-hydroxyglutarate dehydrogenase enzyme, and (v) a cofactor; and b) detecting (D)-2-hydroxyglutarate or (D)-2-hydroxyadipic acid by measuring the production of the reduced state of the dye. The invention further pertains to a method for diagnosing and/or monitoring a (D)-2-hydroxyglutarate-associated disease in a subject. Encompassed by the invention is also a method for diagnosing a mutation in an isocitrate dehydrogenase (IDH) gene and/or in a (D)-2-hydroxyglutarate (D2HG) dehydrogenase enzyme gene in a subject. In addition, the invention provides for a kit comprising (i) a solvent, (ii) a dye having an oxidized state and a reduced state, wherein the reduced state can be distinguished from the oxidized state and wherein the dye is initially present in the oxidized state, (iii) an electron transfer agent, (iv) a (D)-2-hydroxyglutarate dehydrogenase enzyme, and (v) a cofactor.

Isocitrate dehydrogenase (IDH) enzymes catalyze the oxidative decarboxylation of isocitrate to alpha-ketoglutarate in a two-step reaction, resulting in the production of either NADH or NADPH. In humans, three IDH isoforms are known. Two of these isoforms, i.e. the homodimer IDH2 ($NADP^+$-dependent) and the heterotetramer IDH3 ($NAD^+$-dependent) are localized in the mitochondria where they are involved in the Krebs cycle (citrate acid cycle). In contrast thereto, the homodimer IDH1 ($NADP^+$-dependent) is active in the cytosol and the peroxisomes (Geisbrecht et al., 1999, J. Biol. Chem., 274: 30527-30533).

Mutations in genes encoding isocitrate dehydrogenase enzymes have been identified both in neurometabolic disorders and tumorous diseases.

Glutaric aciduria or acidemia type I (glutaryl-CoA dehydrogenase (GCDH) deficiency) is an inherited disorder caused either by mutations in the IDH2 gene encoding the isocitrate dehydrogenase 2 or in the gene encoding the (D)-2-hydroxyglutarate (D2HG)-degrading enzyme, i.e. the D2HG dehydrogenase, resulting in an impairment of the enzymatic functions of said enzymes (Kranendijk et al., 2010, Science 330: 336). In both scenarios, D2HG accumulates in the body of the mutation-carrying patient and is finally excreted with the urine. Glutaric aciduria was first described in 1975 (Goodman et al., 1975, Biochem. Med. 12: 12-21). Retrospective and prospective studies include patients from two North American genetic isolates with a high carrier frequency: The Amish Community (Strauss et al., 2003, Am. J. Med. Genet. 121C: 38-52; Strauss et al., 2007, Brain 130: 1905-1920) and the Saulteaux/Ojibwa (Oji-Cree) Indians (Greenberg et al., 2002, Mol. Gen. Metab. 75: 70-78) as well as European patients (Hoffmann et al., 1991, Pediatrics 88: 1194-1203; Hoffmann et al., 1996, Neuropediatrics 27: 115-123; Busquets et al., 2000, Pediatr. Res. 48: 315-322; Kyllerman et al., 2004, Mov. Disord. 9: 22-30). A metaanalysis of this disease evaluating 42 published case reports describing 115 patients has been reported (Bjugstad et al., 2000, J. Pediatr. 137: 681-686). An international cross-sectional study enrolling 279 patients has also been published (Kölker et al., 2006, J. Pediatr. 137: 681-686). Recently, a guideline for diagnosis and management of glutaric aciduria type I has been introduced (Kölker et al., 2007, J. Inherit. Metab. Dis. 30: 5), and the beneficial effect of using this guideline has been confirmed (Heringer et al., 2010, Ann. Neurol. 68: 743-752). These reports greatly broadened the clinical spectrum of glutaric aciduria type I to include children with nonprogressive extrapyramidal syndromes and even biochemically affected but clinically normal children with glutaric aciduria type I. At present, more than 500 patients have been reported worldwide. As a result, glutaric aciduria is now recognized as one of the most common identifiable inborn errors of metabolism associated with progressive or nonprogressive extrapyramidal disease. In recent years, development of tandem mass spectrometry-based programs for expanded neonatal screening has provided the opportunity to diagnose a variety of children before onset of acute encephalopathy (Lindner et al., 2006, J. Inherit. Metab. Dis. 29: 378-382) and to start prospective follow-up studies (Strauss et al., 2003, loc. cit.; Naughten et al., 2004, J. Inherit. Metab. Dis. 27: 917-920; Kölker et al., 2007, Pediatr. Res. 62: 353-362; Bijarnia et al., 2008, J. Inherit. Metab. Dis. 31: 503-507; Boneh et al., 2008, Mol. Genet. Metab. 94: 287-291).

Succinic semialdehyde dehydrogenase (SSADH) deficiency is another example for a rare inborn error of metabolism primarily revealed by urinary organic acid screening. Patients with proven SSADH deficiency excreted, in addition to gamma-hydroxybutyrate (GHB), considerable amounts of D2HG (Strut's et al., 2006, Molecular Genetics and Metabolism 88(1): 53-57).

In a recent cancer genome sequencing project, heterozygous somatic mutations in the cytosolic isocitrate dehydrogenase 1 (IDH1) have been found primarily in secondary glioblastoma (GBM) (83%) and to a lesser extent in primary GBM (7%) (Parsons et al., 2008, Science 321: 1807-1812). These results could be confirmed by further studies in which IDH1 mutations could frequently be detected in diffused astrocytoma (71%), oligodendrogliomas and oligoastrocytoma of WHO Grade II and III (Balss et al., 2008, Acta Neuropathol., 116: 597-602; Hartmann et al., 2009, Acta Neuropathol., 118: 469-474). In addition, mutations in the mitochondrial isocitrate dehydrogenase (IDH2) have been identified, although with less frequency (3%). IDH mutations occur not only in diffuse gliomas, but also in acute myeloid leukaemia (AML) (IDH1: 6-8.5%; IDH2: 8.7-11%) (Abbas et al., 2010, Blood, 116: 2122-2126; Mardis et al., 2009, New England Journal of Medicine, 361: 1058-1066; Paschka et al., 2010, J. Clin. Oncol., 28: 3636-3643; Schnittger et al., 2010, Blood, 116: 5486-5496), chondrosarcoma (56%) (Amary et al., 2011, J. Pathol., 224: 334-343), intrahepatic cholangiocarcinoma (~25%) (Borger et al., 2012, The Oncologist 17: 72-79) and angioimmunoblastic T cell lymphoma (~45%) (Cairns et al., 2012, Blood).

The mutations occurring in the IDH genes result in an amino acid exchange at two different positions, i.e. at position 100 or 132 in the IDH1 gene, with an arginine to histidine point mutation at position 132 (R132H) representing the most frequent mutation in diffuse gliomas, and at two different positions, i.e. at position 140 or 172, in the IDH2 gene. The mutations are altogether localized in the enzymatic domain in which isocitrate is bound and converted (Soundar and Colman, 2000, J. Biol. Chem., 275: 5606-5612). These site-specific mutations disable the enzymes' normal ability to convert isocitrate to alpha-ketoglutarate (Yan et al., 2009, Cancer Res., 69: 9175-9159; Zhao et al., 2009, Science, 324: 261-265) and confer on the enzymes a new function, i.e. the ability to catalyze the NADPH-dependent reduction of alpha-ketoglutarate to (D)-2-hydroxyglutarate (Dang et al., 2009, Nature, 462: 739-744; Ward et al., 2011, Oncogene, doi:10.1038/onc.2011.416). Other IDH mutations are described in thyroid cancer, however, it is not yet known, whether these mutations result in the production of (D)-2-hydroxyglutarate (Murugan et al., 2010, BBRC 393: 555-559).

The diagnosis of low-grade gliomas is presently performed by the standardized use of the IDH1 R132H-specific antibody. The frequency of this point mutation in said tumorous diseases is about 90%. Therefore, a large number of diffuse glioma incidences can be diagnosed by immunohistological analysis using said antibody (Capper et al., 2009, Acta Neuropathol., 218: 599-601; Capper et al., 2011, International Journal of Cancer/Journal International Du Cancer, doi:10.1002/ijc26425). However, other mutations in the IDH genes can at present only be detected by DNA sequencing of the corresponding exons.

In addition, detection of (D)-2-hydroxyglutarate in tumor tissue and in paraffin-embedded tissues of low-grade gliomas (Sahm et al., 2010, Brain Pathology, doi:10.1111/j.1750-3639.2011.00506.x) and in blood sera of AML patients (Sellner et al., 2010, Eur. J. Haematol., 85: 457-459) can only be carried out by GC-MS (gas chromatography-mass spectrometry) thus far. However, this method is associated with high costs due to the labour-intensive and time-consuming preparation of samples for the analysis. Furthermore, GC-MS is not suitable for high-throughput analysis of samples.

In light of the above, further means and methods for detecting (D)-2-hydroxyglutarate are necessary but not yet available.

In a recent study, cancer-associated mutations from isocitrate dehydrogenases have been applied to homologous residues in the active sites of homoisocitrate dehydrogenases to derive enzymes that catalyze the conversion of 2-oxoadipate to (R)-2-hydroxyadipate, a critical step for adipic acid production (Reitman et al., Nature Chemical Biology (2012) 8: 887-889). In another publication, a biotechnological production process for adipic acid has been postulated (Parthasarathy et al., Biochemistry, 2001 May 3, 50(17): 3540-50; erratum in Biochemistry, 2011 May 24, 50(20): 4392).

Thus, there is also a need for means and methods for monitoring the generation of adipic acid which are not available so far.

Accordingly, the technical problem underlying the present invention can be seen as the provision of means and methods for complying with the aforementioned needs. The technical problem is solved by the embodiments characterized in the claims and herein below.

The invention relates to a method for detecting (D)-2-hydroxyglutarate in a sample, the method comprising the steps of:
a) contacting a sample with a reagent mixture, wherein said reagent mixture comprises:
(i) a solvent,
(ii) a dye having an oxidized state and a reduced state, wherein the reduced state can be distinguished from the oxidized state and wherein the dye is initially present in the oxidized state,
(iii) an electron transfer agent,
(iv) a (D)-2-hydroxyglutarate dehydrogenase enzyme, and
(v) a cofactor; and
b) detecting (D)-2-hydroxyglutarate by measuring the production of the reduced state of the dye.

GC-MS (gas chromatography-mass spectrometry) used commonly for the determination of 2-hydroxyglutarate (2HG) in clinical screening for 2-hydroxyglutarate-associated diseases so far, cannot distinguish between the two enantiomers of 2-hydroxyglutarate, i.e. both enantiomers are being detected by said method. Therefore, the GC-MS has to be followed by a further analysis step using, e.g., a chiral chromatography column for identifying the specific enantiomer. In addition, GC-MS is expensive, mainly due to the labour-intensive and time-consuming preparation of samples for the analysis. So it takes about one and a half day until the results of the GC-MS analysis are available. Furthermore, GC-MS is not suitable for high-throughput analysis of samples.

In contrast thereto, the methods of the present invention provide for simple and robust enzymatic assays for the specific determination of the D- (or R-) enantiomer of 2-hydroxyglutarate, i.e. (D)-2-hydroxyglutarate (D2HG). In addition, said methods are fast since they can be carried out in about 2 to 3 hours. Moreover, they are suitable for 96-well format and can be even further miniaturized to the 384-well format, thereby allowing for the parallel analysis of numerous samples at the same time.

The invention further pertains to a method for detecting (D)-2-hydroxyadipic acid in a sample, the method comprising the steps of:
a) contacting a sample with a reagent mixture, wherein said reagent mixture comprises:
(i) a solvent,
(ii) a dye having an oxidized state and a reduced state, wherein the reduced state can be distinguished from the oxidized state and wherein the dye is initially present in the oxidized state,
(iii) an electron transfer agent,
(iv) a (D)-2-hydroxyglutarate dehydrogenase enzyme, and
(v) a cofactor; and
b) detecting (D)-2-hydroxyadipic acid by measuring the production of the reduced state of the dye.

Recently, a biotechnological production process for adipic acid has been hypothesized by Parthasarathy and co-workers (Parthasarathy et al., Biochemistry, 2001 May 3, 50(17): 3540-50; erratum in Biochemistry, 2011 May 24, 50(20): 4392). Adipic acid is a constituent of the polyamide Nylon-6,6 and several polyesters. Since (D)-2-hydroxyadipic acid is an intermediate in the mentioned biotechnological production process for adipic acid the method for detecting (D)-2-hydroxyadipic acid of the invention can be used, e.g., for monitoring of said process or any other processes for producing adipic acid in which (D)-2-hydroxyadipic acid is being used as an intermediate. For example, it has recently been found that a specific (R)-2-hydroxyadipate dehydrogenase can be obtained by mutating specific residues in the active sites of a homoisocitrate dehydrogenase (Reitman et al., Nature Chemical Biology (2012) 8: 887-889). Said (R)-2-hydroxyadipate dehydrogenase is able to catalyze the conversion of 2-oxoadipate to (R)-2-hydroxyadipate, a critical step for adipic acid production.

In addition, the invention pertains to a method for diagnosing and/or monitoring a (D)-2-hydroxyglutarate-associated disease in a subject, the method comprising:
a) contacting a sample of said subject with a reagent mixture, wherein said reagent mixture comprises:

(i) a solvent, (ii) a dye having an oxidized state and a reduced state, wherein the reduced state can be distinguished from the oxidized state and wherein the dye is initially present in the oxidized state, (iii) an electron transfer agent, (iv) a (D)-2-hydroxyglutarate dehydrogenase enzyme, and (v) a cofactor; and b) detecting (D)-2-hydroxyglutarate by measuring the production of the reduced state of the dye, thereby diagnosing and/or monitoring a (D)-2-hydroxyglutarate-associated disease in said subject.

Preferably, the amount of (D)-2-hydroxyglutarate detected in step b) is compared to a reference amount of (D)-2-hydroxyglutarate from a healthy subject or a cohort of healthy subjects, not carrying a mutation in the IDH1 gene, the IDH2 gene, or the D2HG dehydrogenase enzyme gene. This reference amount is about 6 µM (D)-2-hydroxyglutarate, as determined by GC/MS in sera of healthy subjects having two wildtype alleles of the respective gene. If the amount of (D)-2-hydroxyglutarate in the sample of a tested subject detected in step b) is above this reference amount, this is indicative of a (D)-2-hydroxyglutarate-associated disease in said subject. Since the methods of the invention allow for the specific detection of the D- (or R-) enantiomer of 2-hydroxyglutarate, i.e. (D)-2-hydroxyglutarate (D2HG), said methods can be used for diagnosing and/or monitoring a (D)-2-hydroxyglutarate-associated disease in a subject. In a preferred embodiment, said (D)-2-hydroxyglutarate-associated disease is a tumorous disease selected from the group consisting primarily of diffuse glioma, acute myeloid leukemia (AML), chondrosarcoma, intrahepatic cholangiocarcinoma and angioimmunoblastic T cell lymphoma. Rare cases of (D)-2-hydroxyglutarate-associated thyroid cancer have also been described. Further (D)-2-hydroxyglutarate-associated diseases include non-tumorous glutaric aciduria, succinic semialdehyde dehydrogenase (SSADH) deficiency, Ollier's disease and Maffucci syndrome. Preferably, said diffuse glioma is an astrocytoma WHO grade II (AII), oligodendroglioma WHO grade II (OII) or oligoastrocytoma WHO grade II (OAII). Diffuse gliomas also occur in malignant anaplastic variants containing anaplastic astrocytoma WHO grade III (AIII), anaplastic oligodendroglioma WHO grade III (OIII) and anaplastic oligoastrocytoma WHO grade III (OAIII). All diffuse glioma have the potential to progress to highly malignant secondary glioblastoma.

"Astrocytomas" are gliomas that arise from precursor cells within the brain capable of astrocytic differentiation. It is believed that normal astrocytes derive from these precursor cells. The physiological role of astrocytes is to store information and nutrients for the nerve cells. Oligodendrogliomas are soft, greyish-pink tumors. They often contain solid mineral deposits—which are mostly calcium—called calcifications. "Oligoastrocytomas" as used herein are "mixed glioma" tumors, containing both tumor cells with astrocytic and with oligodendroglial differentiation. Diffuse gliomas are characterized in more detail elsewhere herein. As appreciated by those skilled in the art, said methods of the invention can be used to find or screen further (D)-2-hydroxyglutarate-associated diseases or disorders, for example, tumorous diseases or neurometabolic disorders. Preferably, said diseases or disorders are associated with mutations in IDH and/or D2HG dehydrogenase genes.

The invention further relates to a method for diagnosing a mutation in an isocitrate dehydrogenase (IDH) gene and/or in a (D)-2-hydroxyglutarate (D2HG) dehydrogenase enzyme gene in a subject, the method comprising:

a) contacting a sample of said subject with a reagent mixture, wherein said reagent mixture comprises:

(i) a solvent, (ii) a dye having an oxidized state and a reduced state, wherein the reduced state can be distinguished from the oxidized state and wherein the dye is initially present in the oxidized state, (iii) an electron transfer agent, (iv) a (D)-2-hydroxyglutarate dehydrogenase enzyme, and (v) a cofactor; and b) detecting (D)-2-hydroxyglutarate by measuring the production of the reduced state of the dye, wherein the presence of (D)-2-hydroxyglutarate in the sample of the subject is indicative for a mutation in an isocitrate dehydrogenase (IDH) gene and/or in a (D)-2-hydroxyglutarate dehydrogenase enzyme gene in said subject.

The mutation in an isocitrate dehydrogenase (IDH) gene and/or in a (D)-2-hydroxyglutarate dehydrogenase enzyme gene can be detected, e.g., by DNA sequencing of the corresponding exons in said gene(s) or other methods known in the art.

Preferably, said isocitrate dehydrogenase (IDH) mutation is a mutation in the human IDH1 gene, and/or in the human IDH2 gene and/or in the human D2HG dehydrogenase enzyme gene.

Approximately 70 to 90%, possibly even up to 100%, of diffuse glioma patients (suffering from AII, AIII, OIL OIII, OAII, OAIII, or secondary glioblastoma) carry mutations in the IDH1 and/or IDH2 genes (Parsons et al., 2008, Science 321, 1807-1812; Balss et al., 2008, Acta Neuropathol., 116: 597-602; Hartmann et al., 2009, Acta Neuropathol., 118: 469-474). IDH mutations could also be identified in acute myeloid leukaemia (AML) (IDH1: 6-8.5%; IDH2: 8.7-11%) and angioimmunoblastic T cell lymphoma (Abbas et al., 2010, Blood, 116: 2122-2126; Mardis et al., 2009, New England Journal of Medicine, 361: 1058-1066; Paschka et al., 2010, J. Clin. Oncol., 28: 3636-3643; Schnittger et al., 2010, Blood, 116: 5486-5496; Cairns et al., loc. cit.), chondrosarcoma (56%) (Amary et al., 2011, J. Pathol., 224: 334-343) and intrahepatic cholangiocarcinoma (Borger, loc. cit.). In AML, two cases with mutations in both the IDH1 and IDH2 gene have been described (Abbas et al., loc. cit.). Though very rarely, mutations in IDH have been described in thyroid carcinoma (about 0.1%) and colon carcinoma (Sjöblom et al., 2006, Science 314: 268-274).

Preferably, said mutation is a point mutation as depicted in Table 1 or as described elsewhere herein.

Table 1:

Mutations in IDH1 and IDH2 and their Occurrence in Different Tumorous Diseases.

The amino acid positions at residue (R) 100 and 132 in IDH1 correspond to positions 140 and 172 in IDH2, respectively, since in IDH2, a 40 amino acid mitochondrial signal sequence is present. The occurring amino acid exchanges are in parenthesis, sorted by frequency, i.e. with mutation at the left representing the most frequent mutation.

TABLE 1

|  | IDH1 | | | IDH2 | |
| --- | --- | --- | --- | --- | --- |
|  | R97 | R100 | R132 | R140 | R172 |
| AML | — | — | (C/H/S/V/L/G) | (Q/W) | (W/K/S) |
| Chondrosarcomas | — | — | (C/G/H/L/S) | — | (S) |
| Gliomas | — | (Q) | (H/C/S/V/L/G) | (Q) | (W/K/S) |

AML has been found to be associated with point mutations at position 132 of the IDH1 in which arginine (R) is substituted by cysteine (C), histidine (H), serine (S), valine (V), leucine (L) or glycine (G).

Chondrosarcoma has been found to be associated with point mutations at position 132 of the IDH1 in which arginine (R) is substituted by cysteine (C), glycine (G), histidine (H), leucine (L) or serine (S).

In a colon carcinoma cell line, a point mutation has been identified at position 97 of the IDH1 in which glycine (G) is replaced by aspartic acid (D) (Sjöblom et al., loc. cit.).

Diffuse gliomas have been found to be associated with point mutations (i) at position 100 of the IDH1 in which arginine (R) is replaced by glutamine (Q) and/or (ii) at position 132 of the IDH1 in which arginine (R) is substituted by histidine (H), cysteine (C), serine (S), valine (V), leucine (L) or glycine (G).

The nucleic acid sequence and the amino acid sequence of the human IDH1 is shown in Accession No. NP_005887.2

AML has further been found to be associated with point mutations (i) at position 140 of the IDH2 in which arginine (R) is replaced by glutamine (Q) or tryptophan (W) and/or (ii) at position 172 in which arginine (R) is substituted by tryptophan (W), lysine (K), or serine (S).

Chondrosarcoma has been found to be associated with point mutations at position 172 of the IDH2 in which arginine (R) is replaced by serine (S).

Diffuse gliomas have been found to be associated with point mutations (i) at position 140 of the IDH2 in which arginine (R) is replaced by glutamine (Q) and/or (ii) at position 172 in which arginine (R) is substituted by tryptophan (W), lysine (K), or serine (S).

The nucleic acid sequence and the amino acid sequence of the human IDH2 is shown in Accession No. NP_002159.2.

(D)-2-hydroxyglutaric aciduria is an inherited disorder in which mutations in the IDH2 gene or in the D2HG dehydrogenase gene result in the accumulation of D2HG in the body and in the subsequent excretion of D2HG into the urine. The preferred (D)-2-hydroxyglutarate dehydrogenase enzyme gene is shown in Accession No. NP_689996.4. The preferred mutations are those described by Kranedijk, loc. cit. and by Kölker et al., loc. cit.

Though a large number of diffuse gliomas can be diagnosed by immuno-histological analysis using the IDH1 R132H-specific antibody (Capper et al., 2009, Acta Neuropathol., 218: 599-601; Capper et al., 2011, International Journal of Cancer/Journal International Du Cancer, doi: 10.1002/ijc26425), other mutations in the IDH genes can at present only be detected by DNA sequencing of the corresponding exons. Advantageously, the methods of the invention provide novel and simple assays which allow for a rapid diagnosis of an isocitrate dehydrogenase (IDH) gene mutation and/or D2HG dehydrogenase gene mutation in a subject. Such mutations have been found in tumorous diseases, such as diffuse glioma, AML, angioimmunoblastic T cell lymphoma, chondrosarcoma, intrahepatic cholangiocarcinoma and, rarely, thyroid carcinoma and colon carcinoma; or the neurometabolic disorder glutaric aciduria (type I), for example, (D)-2-hydroxyglutaric aciduria and other diseases and syndromes mentioned elsewhere herein.

As evident to those skilled in the art, the methods of the invention can be used in order to identify further, so far unknown mutations in the above-mentioned genes, such as—without being limiting—additional point mutations, frame shift mutations, nonsense mutations, insertions, deletions or splice variants. To this end, (D)-2-hydroxyglutarate can be detected by measuring the production of the reduced state of the dye by the methods of the invention. The presence of (D)-2-hydroxyglutarate in the sample of the subject is indicative for a mutation in an isocitrate dehydrogenase (IDH) gene and/or in a (D)-2-hydroxyglutarate dehydrogenase enzyme gene in said subject. The corresponding mutation in the isocitrate dehydrogenase (IDH) gene or in a (D)-2-hydroxyglutarate dehydrogenase enzyme gene can be identified, for example, by sequencing the exons of said gene. Sequencing is well known in the art; see, e.g. Molecular cloning: A laboratory manual/Sambrook, Joseph; Russell, David W., 3rd ed., New York: Cold Spring Harbor Laboratory, 2001.

A "point mutation" as used herein means an exchange of a single nucleotide for another. In the translated protein, said nucleotide exchange may result in an amino acid exchange which can be classified in (i) a silent mutation in which the nucleotide exchange codes for the same amino acid, (ii) a missense mutation in which the nucleotide exchange codes for a different amino acid or (iii) a nonsense mutation in which the nucleotide exchange codes for a stop codon which can truncate the protein. "Insertions" as used herein add one or more extra nucleotides into the DNA. Insertions in the coding region of a gene may alter splicing of the mRNA (splice site mutation), or cause a shift in the reading frame (frameshift), both of which can significantly alter the gene product. "Deletions" as used herein remove one or more nucleotides from the DNA. Like insertions, these mutations can alter the reading frame of the gene.

The term "2-hydroxyglutarate" (2HG) or "2-hydroxyglutaric acid" or "alpha-hydroxyglutaric acid" as referred to herein is an alpha-hydroxy acid. The corresponding CAS number is 2889-31-8. In humans, the compound is formed by a hydroxyacid-oxoacid transhydrogenase, whereas in bacteria it is formed by a 2-hydroxyglutarate synthase. The compound can be converted to alpha-ketoglutaric acid through the action of a 2-hydroxyglutarate dehydrogenase which, in humans, are two enzymes called D2HGDH and L2HGDH. Deficiency in either of these two enzymes leads to a neurometabolic disease known as 2-hydroxyglutaric aciduria, as set forth in more detail elsewhere herein.

The term "(D)-2-hydroxyglutarate" or "(D)-2-hydroxyglutaric acid" or "D2HG" or "(R)-2-hydroxyglutarate" or "(R)-2-hydroxyglutaric acid" as used herein means the D-stereoisomer of 2-hydroxydglutaric acid. The corresponding CAS number is 636-67-9. Tissue accumulation of high amounts of (D)-2-hydroxyglutaric acid is the biochemical hallmark of the inherited neurometabolic disorder "(D)-2-hydroxyglutaric aciduria". The main features of (D)-2-hydroxyglutaric aciduria are developmental delay, seizures, weak muscle tone (hypotonia), and abnormalities in the largest part of the brain (the cerebrum), which controls many important functions such as muscle movement, speech, vision, thinking, emotion, and memory. Symptoms of (D)-2-hydroxyglutaric aciduria can be severe or mild. Onset of the severe form usually occurs before the age of 6 months. In addition to the main features of this disorder, signs and symptoms of the severe form usually include lack of energy (lethargy), episodes of vomiting, facial abnormalities such as a prominent forehead or very small lower jaw (micrognathia), vision problems, a weakened and enlarged heart (cardiomyopathy), and breathing abnormalities. Onset of the mild form of (D)-2-hydroxyglutaric aciduria typically occurs between ages 6 months and 3 years. Symptoms of this form are variable but usually include seizures and minor delays in development. In rare cases, symptoms are so mild that no abnormalities are noticed.

Combined (D)-2-hydroxyglutaric aciduria is encompassed by the term "(D)-2-hydroxyglutaric aciduria" as used herein.

(D)-2-hydroxyglutarate is also produced in patients suffering from diffuse gliomas, AML, angioimmunoblastic T cell lymphoma, chondrosarcoma, intrahepatic cholangiocarcinoma and, though less frequently, thyroid carcinoma or colon carcinoma. As set forth elsewhere herein, mutations in the isocitrate dehydrogenase gene IDH1 and/or IDH2 are a common feature of said tumorous diseases. The methods of the present invention can be used in order to diagnose the above-mentioned disorders and/or mutations in the IDH genes or D2HG dehydrogenase genes, by specifically detecting (D)-2-hydroxyglutarate.

The term "(L)-2-hydroxyglutaric acid" or "(L)-2-hydroxyglutarate" or "(S)-2-hydroxyglutaric acid" or "(S)-2-hydroxyglutarate" as used herein means the L-stereoisomer of 2-hydroxyglutaric acid. The corresponding CAS number is 13095-48-2. (L)-2-hydroxyglutaric acid is a metabolite that accumulates in "L-2-hydroxyglutaric aciduria" (a neurometabolic disorder, OMIM 236792), and has been reported in multiple patients who have a clinical phenotype of progressive neurodegeneration with extrapyramidal and cerebellar signs, seizures, and spongiform changes in the white matter (OMIM 600721) and Spondyloenchondrodysplasia (OMIM 271550). (L)-2-hydroxyglutaric aciduria also damages the brain, particularly the region involved in coordinating movements, the cerebellum. As a result, affected individuals have problems with balance and muscle coordination (ataxia). Additional signs and symptoms include intellectual disability, seizures, impaired speech, short stature, and an unusually large head (macrocephaly). Typically, signs and symptoms of this disorder begin during infancy or early childhood. Symptoms of (L)-2-hydroxyglutaric aciduria usually progress slowly, but severe disability occurs by early adulthood. In some cases, the onset of symptoms is delayed until adolescence or adulthood, and the symptoms tend to be milder compared to cases that begin during infancy.

Combined (D)-2-hydroxyglutaric aciduria and (L)-2-hydroxyglutaric aciduria has been reported in a small number of infants. Signs and symptoms are severe and occur within the first month of life.

The chirality of 2HG in a sample can be assessed or confirmed by methods known in the art, for example, by diacetyl-L-tartaric anhydride derivatization and LC-MS analysis, as described in Dang et al., 2009, loc. cit. For example, to determine the chirality of the 2HG in a sample, the 2HG can be derivatized with diacetyl-L-tartaric anhydride, which then allows to separate the (S) and (R) enantiomers of 2HG by reverse-phase LC and to detect the products by tandem mass spectrometry. The peaks corresponding to the (S) and (R) isomers of 2HG can be confirmed, e.g., by using racemic and (R)-2HG or (S)-2HG standards. Further methods which can be used to determine specifically which of the 2HG or 2-hydroxyadipic acid enantiomer(s) is/are present in a sample include GC-MS, HPLC or MS.

The terms "alpha-ketoadipic acid" or "2-oxoadipate" or "2-oxohexanedioic acid" as used herein is an intermediate in the metabolism of lysine and tryptophan. The corresponding CAS number is 3184-35-8. Further information to alpha-ketoadipic acid can be found, e.g., in Parthasarathy et al., Biochemistry, 2001 May 3, 50(17): 3540-50; erratum in Biochemistry, 2011 May 24, 50(20): 4392. Briefly, it has inter alia been analyzed in this study whether the three enzymes, 2-hydroxyglutarate dehydrogenase and glutaconate CoA-transferase from *Acidaminococcus fermentans* as well as 2-hydroxyglutaryl-CoA dehydratase from *Clostridium symbiosum* can convert 2-oxoadipate to 2-hexenedioic acid. Reduction of this unsaturated dicarboxylic acid would lead to adipic acid (hexanedioic acid) that is chemically produced from benzene at a world scale of 2.4 million tons in 2008. Adipic acid is a constituent of the polyamide Nylon-6,6 and several polyesters.

The term "(D)-2-hydroxyadipic acid" or "(R)-2-hydroxyadipic acid" or "(D)-2-hydroxyadipate" or "(R)-2-hydroxyadipate" as used herein is the D (or R) stereoisomer of 2-hydroxyadipic acid (2-hydroxyadipate or 2-hydroxyhexanedioic acid), the CAS number of which is 18294-85-4. Interestingly, it has been found in a recent study, that the levels of 2-hydroxyadipic acid and 2-hydroxyglutaric acid were lower in urine of IL10$^{-/-}$ mice compared to wildtype mice (Lin et al, Journal of Proteome Research (2009), 8, 2045-2057). (D)-2-hydroxyadipic acid is generated from (2R,3S)-homoisocitrate, an intermediate in the biosynthesis of lysine in fungi, by the homoisocitrate dehydrogenase in an NADPH-dependent reaction. Further, it is an intermediate in a postulated bio-based production assay of adipic acid; see Parthasarathy et al., loc. cit. Further information can be found in Reitman et al., Nature Chemical Biology (2012) 8: 887-889.

The term "diagnosing" according to the methods of the present invention includes detecting, monitoring, confirmation, sub-classification, and prediction of the (D)-2-hydroxyglutarate-associated disease set forth herein, the symptoms or risks for it. The term "detecting" as used herein means to discover or ascertain the existence or presence of (D)-2-hydroxyglutarate or a (D)-2-hydroxyglutarate-associated disease or (D)-2-hydroxyadipic acid as referred to herein. To this end, for instance, the amount of (D)-2-hydroxyglutarate can be measured by the methods of the invention in a sample of a subject supposed to suffer from a (D)-2-hydroxyglutarate-associated disease, as demonstrated in the following examples. The term "monitoring" as used herein relates to keeping track of an already diagnosed (D)-2-hydroxyglutarate-associated disease or complication, e.g. to analyzing the progression or consequence of the disease or the influence of a particular treatment on the progression of disease or complication. For example, said monitoring comprises screening for the modulation of the level or amount of (D)-2-hydroxyglutarate in a patient's sample in order to detect and/or follow a tumorous disease or a neurometabolic disease as referred to herein. Said modulation of the level or amount of (D)-2-hydroxyglutarate (D2HG) can be, for example, an increase or decrease of the amount of the mentioned compound. Preferably, the increase or decrease is a modulation of at least 5%, 10%, 15%, 20%, 25%, 30%, or even more, in comparison to the amount of said compound determined at a previous time point. For example, the amount of D2HG can be determined at various time points (T) T0, T1, T2, T3 and so forth, in order to determine or follow the efficacy of a therapy. A statistically significant increase of the amount of D2HG in a sample of a patient suffering from a D2HG-associated disease as referred to herein can be indicative of a worsening of said disease or can be a sign of a relapse of said disease. A statistically significant decrease of the amount of D2HG in a sample of a patient suffering from a D2HG-associated disease as referred to herein can be indicative of an improvement of said disease, for example, by the appropriate treatment of said disease. Whether an increase or decrease in the amount of D2HG is statistically significant can be determined by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York, 2004. Preferred confidence intervals are at least 90%, at least 95%, at least 96%, at least 97%, at least 98% or at least 99%. The p-values are, preferably, 0.1, 0.05, 0.01, 0.005, or 0.0001. (D)-2-hydroxyadipic acid can be used as an intermediate in biotechnological production processes for adipic acid. Accordingly, the method for detecting (D)-2-hydroxyadipic acid of the invention can be utilized, e.g., for monitoring of said biotechnological production processes or any other processes for producing adipic acid in which (D)-2-hydroxyadipic acid is being used as an intermediate. "Confirmation" relates to the strengthening or substantiating a diagnosis already performed using typical symptoms of the respective disease or other indicators or markers. "Sub-classification" relates to further defining a diagnosis according to different sub-classes of the diagnosed disease, e.g., defining according to mild and severe forms of the disease. "Prediction" relates to the prognosis of a disease or complication before other symptoms or markers have become evident or have become significantly altered.

The term "subject" as used herein relates to animals, preferably mammals, and, more preferably, humans. It is preferred that the subject is a human patient supposed to suffer or suffering from a (D)-2-hydroxyglutarate-associated disease as referred to herein. The human patient can be an adult patient aged more than 18 years but also a pediatric patient aged 18 years or less than 18 years. The term "pediatric patient" as referred to herein comprises also newborns. A newborn is an infant who is within hours, days, or up to a few weeks from birth. In a medical context, newborn or neonate often refers to a baby in the first 28 days after birth. "Pediatric patient" as used herein further comprises children aged up to and including 18 years. The children may be more specifically sub-grouped into infants (1 month to 12 months of age), younger children aged 1 to 9 years, and older children and adolescents (10 to 18 years of age). The term "infant" is derived from the Latin word infans, meaning "unable to speak" or "speechless." It is typically applied to children between the ages of 1 month and 12 months; however, definitions vary between birth and 3 years of age. The human development stage before infancy is described as prenatal or fetal.

As used herein, a time interval which is defined as "X to Y" equates with a time interval which is defined as "between X and Y". Both time intervals specifically include the upper limit and also the lower limit. This means that, for example, a time interval "from one month to 12 months of age" includes "one month" and "12 months" and any time interval in between. This definition applies mutatis mutandis to any numerical ranges indicated herein such as concentration ranges, pH ranges, volume ranges and the like.

The methods of the invention can advantageously be used as an enzymatic test during pregnancy on cells from the fetus in order to determine whether the fetus suffers from a (D)-2-hydroxyglutarate-associated disease. The sample of the fetus needed for this test can be obtained, e.g., by either chorionic villus sampling (CVS) or amniocentesis. In addition, said methods of the invention can be utilized for newborn screening in order to analyze whether a newborn has a (D)-2-hydroxyglutarate-associated disease. Further, since a number of tumorous diseases are associated with the production of (D)-2-hydroxyglutarate due to mutations in IDH or D2HG dehydrogenase genes, the methods of the invention can be used for diagnosing and/or monitoring, e.g., diffuse gliomas, chondrosarcomas, acute myeloid leukaemia (AML), angioimmunoblastic T cell lymphoma, intrahepatic cholangiocarcinoma or thyroid or colon carcinoma. In addition, said methods of the invention can be used to find further tumorous diseases or neurometabolic diseases which are associated with mutations in the mentioned genes.

The term "tumor" or "tumorous disease" or "tumorous disorder" as used herein refers to an abnormal mass of tissue that results when cells divide more than they should, for example due to deregulated proliferation, or do not die when they should, for example due to deregulated apoptosis. Tumors may be benign (not cancer), or malignant (cancer). Tumors are also called neoplasm. Preferably, the term "tumor" or "tumorous disease" or "tumorous disorder" as referred to herein comprise gliomas, more preferably, diffuse gliomas, chondrosarcomas, acute myeloid leukaemia (AML), angioimmunoblastic T cell lymphoma, intrahepatic cholangiocarcinoma and thyroid or colon carcinoma. As evident to those skilled in the art, further tumors may be identified in the future by the means and methods of the invention which carry mutations in IDH1 and/or IDH2 and/or in D/L2HGDH genes.

A "diffuse glioma" as referred to herein refers to all neoplastic cell growth that arises from glial cells or their precursors of the brain or the spinal cord. Gliomas are histologically classified based on whether they exhibit primarily astrocytic or oligodendroglial morphology, and are graded by cellularity, nuclear atypia, necrosis, mitotic figures, and microvascular proliferation—all features associated with biologically aggressive behavior. Gliomas can manifest in different morphologies (basis for classification) and in different grades ranging from WHO grade I to WHO grade IV and exhibiting clinical behavior from benign via semi-malignant to malignant to highly malignant. Benign gliomas show little infiltration of the brain and exhibit slow growth and usually are graded according to WHO grade I. Among others, this group includes juvenile pilocytic astrocytoma. Semi-malignant gliomas include the diffuse astrocytomas, oligodendrogliomas and oligoastrocytomas of WHO grade II, which infiltrate diffusely and exhibit moderate growth rates. Malignant gliomas include the anaplastic versions of astrocytomas, oligodendrogliomas and oligoastrocytomas all graded WHO grade III exhibiting also diffuse infiltration and substantial growth. Highly malignant gliomas include the primary and secondary glioblastomas WHO grade IV.

In 2007, the WHO ratified the newest version of a comprehensive classification of neoplasms affecting the central nervous system. The classification of brain tumors is based on the premise that each type of tumor results from the abnormal growth of a specific cell type. To the extent that the behavior of a tumor correlates with a basic cell type, the tumor classification dictates the choice of therapy and predicts prognosis. The new WHO system is particularly useful in this regard with only a few notable exceptions (for example, all or almost all gemistocytic astrocytomas are actually anaplastic and hence grade III or even IV, rather than grade II as designated by the WHO system). The WHO classification also provides a parallel grading system for each type of tumor. In this grading system, most named tumors are of a single defined grade. The WHO classification provides the standard for communication between different centers in the United States and around the world. An outline of this classification is provided below.

According to the WHO classification, gliomas are classified into four grades (WHO grade I, II, III, and IV) and the treatment and prognosis depend upon the tumor grade (Claus and Black, 2006, Cancer, 106: 1358). The more common sub-types are: Diffuse astrocytomas. These tumors are usually diagnosed in individuals in their late thirties. Pilocytic astrocytomas are tumors which occur mostly in people who are younger than 25 years of age. Oligodendrogliomas are tumors which can be slow growing tumors. Mixed gliomas consist of mixtures of various tumor sub-types, e.g., diffused astrocytoma and oligodendroglioma. These tumors tend to behave similarly to diffuse astrocytomas. Diffuse glioma as referred to herein preferably mean astrocytoma WHO grade II, anaplastic astrocytoma WHO grade III, oligodendroglioma WHO grade II, anaplastic oligodendroglioma WHO grade III, oligoastrocytoma WHO grade II, anaplastic oligoastrocytoma WHO grade III and secondary glioblastoma WHO grade IV.

Astrocytic glioma can be classified according to the WHO system as follows: Astrocytoma WHO grade II with protoplasmic, gemistocytic, fibrillaryvariants, anaplastic (malignant) astrocytoma WHO grade III which may be further categorized in hemispheric, diencephalic, optic, brain stem, and cerebellar, primary and secondary glioblastoma WHO grade IV with giant cell glioblastoma and gliosarcoma variants, pilocytic astrocytoma WHO grade I which may be further categorized in hemispheric, diencephalic, optic, brain stem, and cerebellar; subependymal giant cell astrocytoma WHO grade I and pleomorphic xanthoastrocytoma WHO grade I.

Oligodendroglialglioma can be classified according to the WHO system as follows: Oligodendroglioma WHO grade II and anaplastic oligodendroglioma WHO grade III, oligoastrocytoma WHO grade II and anaplastic oligoastrocytoma WHO grade III. The terms oligoastrocytoma and mixed glioma are used as synonyms.

Ependymalglioma can be classified according to the WHO system as follows: Ependymoma WHO grade II with cellular, papillary, epithelial, clear cell, and mixed variants, anaplastic ependymoma WHO grade II, myxopapillary ependymoma WHO grade I and subependymoma WHO grade I.

Glioma of uncertain lineage can be classified according to the WHO system as follows: Polar spongioblastoma WHO grade IV, astroblastoma WHO grade IV and gliomatosis cerebri WHO grade IV.

Tumors of the choroid plexus can be classified according to the WHO system as follows: Choroid plexus papilloma, choroid plexus carcinoma (anaplastic choroid plexus papilloma).

Neuronal and mixed neuronal-glial tumors can be classified according to the WHO system as follows: Gangliocytoma, dysplastic gangliocytoma of cerebellum (Lhermitte-Duclos), ganglioglioma, anaplastic (malignant) ganglioglioma, desmoplastic infantile ganglioglioma including desmoplastic infantile astrocytoma, dentral neurocytoma, dysembryoplastic neuroepithelial tumor, olfactory neuroblastoma (esthesioneuroblastoma) including olfactory neuroepithelioma.

Pineal tumors can be classified according to the WHO system as follows: Pineocytoma, pineoblastoma and pineal parenchymal tumor of intermediate differentiation, papillary tumor of the pineal region.

Embryonal tumors can be classified according to the WHO system as follows: Medulloepithelioma, primitive neuroectodermal tumors with multipotent differentiation including medulloblastoma with medullomyoblastoma, melanocytic medulloblastoma, and desmoplastic medulloblastoma variants, and cerebral primitive neuroectodermal tumor; neuroblastoma including the ganglioneuroblastoma variant, retinoblastoma and ependymo-blastoma.

Gliomas may also be subclassified as invasive or non-invasive, although this is not formally part of the WHO system, the non-invasive tumor types are indicated below.

Other CNS neoplasms include tumors of the sellar region comprising pituitary adenoma, pituitary carcinoma and craniopharyngioma; hematopoietic tumors comprising primary malignant lymphomas, plasmacytoma and others. Germ cell tumors comprising germinoma, embryonal carcinoma, yolk sac tumor (endodermal sinus tumor), choriocarcinoma, teratoma and mixed germ cell tumors. Tumors of the meninges comprising meningioma including meningothelial, fibrous transitional, psammomatous, angiomatous, microcystic, secretory, clear cell, chordoid, lymphoplasmacyte-rich, metaplastic subtype variants, atypical meningioma and anaplastic (malignant) meningioma. Non-menigothelial tumors of the meninges including osteocartilaginous tumors, lipoma, fibrous histiocytoma and others. Malignant mesenchymal tumors including chondrosarcoma, hemangiopericytoma, rhabdomyosarcoma, meningeal sarcomatosis and others. Primary melanocytic lesions including diffuse melanosis melanocytoma and malignant melanoma with variant meningeal melanomatosis. Hemopoietic neoplasms including malignant lymphoma, plasmactoma and granulocytic sarcoma. Tumors of uncertain histogenesis including hemangioblastoma (capillary hemangioblastoma). Tumors of cranial and spinal nerves comprising schwannoma (neurinoma, neurilemoma) including cellular, plexiform and melanotic subtypes, neurofibroma including circumscribed (solitary) neurofibroma and plexiform neurofibroma, malignant peripheral nerve sheath tumor including epitheloid, in divergent mesenchymal or epithelial differentiation and melanotic variants. Local extensions from regional tumors comprising paraganglioma (chemodectoma), chordoma, chondroma, chondrosarcoma and carcinoma. Metastatic tumours. Unclassified tumors. Cysts and tumor-like lesions comprising Rathke cleft cyst, epidermoid, dermoid, colloid cyst of the third ventricle, enterogenous cyst, neuroglial cyst, granular cell tumor choristoma, pituicytoma, hypothalamic neuronal hamartoma, nasal glial herterotopia and plasma cell granuloma.

A number of other grading systems are in common use for tumors of the astrocytic lineage (i.e. astrocytomas, anaplastic astrocytomas and glioblastomas), such as the St. Anne/Mayo or the Kernohan grading system. In these systems, grades are assigned solely based on the microscopic appearance of the tumor. The numerical grade assigned for a given tumor, however, can vary depending on which grading system is used. Thus, it is important to specify the grading system referred to when a grade is specified. The St Anne/Mayo grade has proven to correlate better with survival than the previously common Kernohan grading system. It can only be applied to invasive tumors of astrocytic lineage; otherwise it is similar to the WHO grading system.

Briefly, the WHO grading of astrocytic tumors as referred to herein may be summarized as follows:
Pilocytic astrocytoma: WHO grade I
Astrocytoma: WHO grade II
Anaplastic (malignant) astrocytoma: WHO grade III
Glioblastoma: WHO grade IV Diagnosis and therapy of diffuse glioma are known in the art (Ferroli et al., 2010, World Neurosurg 73: 234-236; Hartmann et al., 2011, Clinical Cancer Research 17: 4588-4599; Mukasa et al., Cancer Science: doi:10.1111/j.1349-7006.2011.02175.x; Sanai, Chang & Berger, 2011, Journal of Neurosurgery 115: 948-965; Sherman, Weintraub, Lopes & Schiff, 2011, Primary Central Nervous System Tumors, pp. 173-194, at <http://www.springerlink.com/content/nrw13t1501v1wg33/>; Soffietti et al., 2010, European Journal of Neurology 17: 1124-1133; Thon et al., 2012, Cancer 118: 452-460; van den Bent et al., 2010, Clinical Cancer Research 16: 1597-1604; Weller, 2011, Swiss Med Wkly 141, w13210).

The term "acute myeloid leukaemia" (AML), also known as "acute myelogenous leukemia", as used herein, is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Approximately 12.000 adults are diagnosed with acute myeloid leukemia (AML) in the United States annually, with a median age of 67 years. Despite advances in therapeutics and supportive care, the majority of patients with AML die from their disease. Acute promyelocytic leukemia, which comprises about 10% of adults with AML, is an important exception to this general statement. In this subtype, not considered in detail here, more than 75% of patients are cured with a combination of anthracycline-based chemotherapy, all-trans retinoic acid, and arsenic trioxide. For some APL patients, it is possible to eliminate cytotoxic chemotherapy altogether and to achieve cure with arsenic and all-trans retinoic acid alone. For all other subtypes of AML, the mainstay of initial treatment was developed nearly 40 years ago as a combination of cytosine arabinoside (ara-C) with an anthracycline, and this regimen remains the worldwide standard of care. Approximately 70%-80% of patients less than 60 years of age will achieve complete remission, but most ultimately relapse and overall survival is only 40%-45% at 5 years. Among patients more than 60 years of age, 40%-50% of those with a good performance status can achieve complete remission, but cure rates are less than 10% and median survival is less than 1 year. The outlook for older AML patients has not changed in 3 decades, and is even worse for older patients with unfavorable cytogenetics and/or poor performance status.

In the last few years, there have been several practice-changing developments in the diagnosis and treatment of AML. The old "favorable, intermediate, and unfavorable" prognostic categories, which were based on cytogenetic risk groups, are no longer adequate. Advances in genomics technologies have identified AML as a genetically highly heterogeneous disease, and an increasing number of AML patients can now be categorized into distinct clinic-pathologic subgroups on the basis of their underlying molecular genetic defects. Cytogenetically normal patients, who comprise the largest subgroup and have historically been assigned an "intermediate" prognosis, can now be further divided into a myriad of molecular subgroups, some of which are known to have significant prognostic implications. For example, mutations in FLT3-ITD (FML-like tyrosine kinase 3 internal tandem duplication) have been associated with an aggressive disease phenotype and poor outcomes. In contrast, patients with biallelic mutations in CEBPA (CCAAT enhancer-binding protein alpha) and NPM1 (nucleophosmin 1) without concomitant mutations in FLT3-ITD have significantly more favorable outcomes. Prognostically important mutations have also been identified in patients with abnormal cytogenetics; for example, mutations in KIT may negate the "favorable" classification previously associated with t(8;21). Only FLT3-ITD, NPM1, and biallelic CEBPA mutations have been incorporated in into AML clinical practice guidelines so far.

Diagnosis and therapy of AML are known in the art (Chou et al., 2011, Leukemia at <http://dx.doi.org/10.1038/leu.2011.215>; Damm et al., 2011, Leukemia 25: 1704-1710; Döhner & Gaidzik, 2011, ASH Education Program Book, pp. 36-42; Georgiou et al., 2011, Leukemia at <http://dx.doi.org/10.1038/leu.2011.280>; Rakheja et al., 2011, British Journal of Haematology 155: 125-128; Ravandi et al., Cancer: doi:10.1002/cncr.26580).

The term "chondrosarcoma" herein is used for a type of mesenchymal neoplasm originating from cartilagenous tissue or precursors thereof. Chondrosarcomas are graded according to the FNCLCC (French Federation Nationale des Centre des Lutte Contre le Cancer) grading system which is a modification of the Coindre classification system for sarcomas. Chondrosarcomas occur in different malignancy grades and in different variants. Therapy relies on surgery, radiation and chemotherapy, however the long term success of therapy is poor. Presence of IDH mutations in a fraction of chondrosarcoma make them candidates for targeted therapy. The increased (D)-2-hydroxyglutarate levels in chondrosarcoma with IDH mutation make them candidates for biochemical testing.

The term "cholangiocarcinoma" herein is used for a type of carcinoma originating from the bile ducts in the liver. The tumors of the biliary tract include pancreatic cancer, gallbladder cancer and ampulla of Vater cancer. Therapy of cholangiocarcinoma relies on surgery, chemotherapy and irradiation. Unless complete surgical excision is carried out, the therapeutic success is poor. Presence of IDH mutations in a fraction of cholangiocarcinoma, in particular intrahepatic cholangiocarcinoma, make them candidated for targeted therapy. The increased (D)-2-hydroxyglutarate levels in cholangiocarcinoma with IDH mutation make them candidates for biochemical testing.

The term "angioimmunoblastic T cell lymphoma" (AITL) as used herein refers to a rare and complex lymphoproliferative disorder, clinically characterized by widespread lymphadenopathy, extranodal disease, immune-mediated hemolysis and polyclonal hypergammaglobulinemia. Significant progress has been made in the understanding of AITL since its recognition as a clonal T cell disorder with associated deregulation of B cells and endothelial cells within a unique malignant microenvironment. However, as the responses to conventional chemotherapy have not been durable, prognosis with current treatment approaches has remained dismal. Originally described in 1974 as "immunoblastic lymphadenopathy" by Rappaport and Lukes, angioimmunoblastic T cell lymphoma (AITL) is recognized in the current World Health Organization (WHO) classification as a peripheral T cell lymphoma (PTCL) with distinct clinicopathologic features. Globally, AITL represents approximately 20% of all PTCLs and accounts for roughly 2-5% of non-Hodgkin lymphomas (NHLs), with significant geographic variation in distribution and incidence. In a report by the International T Cell Lymphoma Study Group, AITL was found to be more prevalent in Europe, where it accounted for 28% of PTCL cases, compared to 15% in North America and 17% in Asia (Alizadeh and Advani, 2008, Clin. Advances in Hematol. and Oncol. 6(12): 899-909).

The term "thyroid carcinoma" as used herein is a thyroid neoplasm that is malignant. It can be treated with radioactive iodine or surgical resection of the thyroid gland. Chemotherapy or radiotherapy may also be used.

The term "colon carcinoma" as used herein refers to colon or colorectal cancer that starts in the large intestine (colon) or the rectum (end of the colon). According to the American Cancer Society, colorectal cancer is one of the leading causes of cancer-related deaths in the United States. However, early diagnosis often leads to a complete cure. Almost all colon cancer starts in glands in the lining of the colon and rectum. There is no single cause of colon cancer. Nearly all colon cancers begin as noncancerous (benign) polyps, which slowly develop into cancer. Certain genetic syndromes also increase the risk of developing colon cancer. Two of the most common are familial adenomatous polyposis (FAP) and hereditary nonpolyposis colorectal cancer (HNPCC). Many cases of colon cancer have no symptoms. The following symptoms, however, may indicate colon cancer: abdominal pain and tenderness in the lower abdomen, blood in the stool, diarrhea, constipation, or other change in bowel habits, narrow stools, and weight loss with no known reason. With proper screening, colon cancer can be detected before symptoms develop, when it is most curable. A fecal occult blood test (FOBT) may detect small amounts of blood in the stool, which could suggest colon cancer. However, this test is often negative in patients with colon cancer. For this reason, a FOBT must be done along with colonoscopy or sigmoidoscopy. Stages of colon cancer are: stage 0: very early cancer on the innermost layer of the intestine; stage I: cancer is in the inner layers of the colon; stage II: cancer has spread through the muscle wall of the colon; stage III: cancer has spread to the lymph nodes; stage IV: cancer has spread to other organs. Blood tests to detect tumor markers, including carcinoembryonic antigen (CEA) and CA 19-9, can also be used for diagnosis. Treatment of colon carcinoma depends partly on the stage of the cancer. In general, treatments may include: surgery (most often a colectomy) to remove cancer cells, chemotherapy to kill cancer cells and radiation therapy to destroy cancerous tissue. Stage 0 colon cancer may be treated by removing the cancer cells, often during a colonoscopy. For stages I, II, and III cancer, more extensive surgery is needed to remove the part of the colon that is cancerous. There is some debate as to whether patients with stage II colon cancer should receive chemotherapy after surgery. Almost all patients with stage III colon cancer should receive chemotherapy after surgery for approximately 6 to 8 months. The chemotherapy drug 5-fluorouracil has been shown to increase the chance of a cure in certain patients. Chemotherapy is also used to improve symptoms and prolong survival in patients with stage IV colon cancer. Irinotecan, oxaliplatin, capecitabine, and 5-fluorouracil are the three most commonly used drugs. Monoclonal antibodies, including cetuximab (Erbitux), panitumumab (Vectibix), bevacizumab (Avastin), and other drugs have been used alone or in combination with chemotherapy. Although radiation therapy is occasionally used in patients with colon cancer, it is usually used in combination with chemotherapy for patients with stage III rectal cancer. For patients with stage IV disease that has spread to the liver, various treatments directed specifically at the liver can be used. This may include: burning the cancer (ablation), delivering chemotherapy or radiation directly into the liver, freezing the cancer (cryotherapy), or surgery.

The term "relapsed or recurrent" as used herein denotes the return of signs and symptoms of the (D)-2-hydroxyglutarate-associated disease after a patient has enjoyed a remission. For example, after conventional tumor treatment using chemotherapy and/or human stem cell transplantation in AML, a tumor patient may go into remission with no sign or symptom of the tumor, remains in remission for a couple of years, but then suffers a relapse and has to be treated once again for the tumor. Accordingly, in specific embodiments, the methods of the invention can be used for detecting a relapse of the tumorous disease as referred to herein or metastases originating from primary tumors.

Another (D)-2-hydroxyglutarate-associated disease which can be detected, diagnosed or monitored by the methods of the invention is (D)-2-hydroxyglutaric aciduria. This disease is an inherited disorder in which mutations in the IDH2 gene result in the production of D2HG. Other mutations in the D2HG dehydrogenase gene result in a functionally impaired enzyme which result also in the accumulation of D2HG in the body. In both cases, D2HG is excreted with the urine.

Other metabolic disorders exhibiting mildly elevated D2HG include multiple acyl-CoA dehydrogenase deficiency, dihydrolipoyl dehydrogenase deficiency, pyruvate decarboxylase deficiency and pyruvate carboxylase deficiency. Also these disorders can be detected, diagnosed or monitored by the methods of the invention.

The term "treatment" as used herein means in the broadest sense medical procedures or applications that are intended to relieve the (D)-2-hydroxyglutarate-associated disease referred to herein.

The term "amelioration" as used herein is synonymous with improvement. If a patient's condition suffering from a (D)-2-hydroxyglutarate-associated disease as referred to herein shows amelioration, the patient is clearly better—there is some improvement in her or his clinical condition. For example, it may be an improvement in the patient's condition, if a stabilization of said disease can be achieved, i.e. the disease is no longer progressive. This disease stage is also termed stable disease.

The term "sample" as used herein refers to a cell-free sample or a sample comprising cells, such as a sample of a body fluid, a sample of isolated and/or separated cells, cell lysates or cell (culture) supernatants or a sample from a tissue or an organ, including biopsies or tissue sections. Samples of body fluids can be obtained by well known techniques and include, preferably, samples of blood, plasma, serum or urine. Tissue or organ samples may be obtained from any tissue or organ, e.g., by biopsy. Isolated and/or separated cells may be obtained from the body fluids or the tissue or organs by separating techniques such as centrifugation or cell sorting (FACS). The sample can be frozen or paraffin-embedded. Preferably, the sample used in the methods of the invention is a blood sample, serum sample, plasma sample, urine sample, or a biopsy of tumor tissues of the tumors referred to herein or a tissue section. The sample is preferably from a subject as defined herein. For example, the sample can be derived from a newborn, a pediatric patient or an adult patient as defined herein. The sample can also be derived from a fetus which can be obtained, e.g., by either CVS or amniocentesis.

The term "determining the amount of (D)-2-hydroxyglutarate (D2HG)" or "determining the amount of (D)-2-hydroxyadipic acid" referred to herein relates to measuring the amount or concentration of D2HG or (D)-2-hydroxyadipic acid, preferably semi-quantitatively or quantitatively. Measuring can be done directly or indirectly. Direct measuring relates to measuring the amount or concentration of D2HG or (D)-2-hydroxyadipic acid based on a signal which is obtained from D2HG or (D)-2-hydroxyadipic acid itself and the intensity of which directly correlates with the number of molecules of D2HG or (D)-2-hydroxyadipic acid present in the sample. Such a signal may be obtained, e.g., by measuring an intensity value of a specific physical or chemical property of D2HG or (D)-2-hydroxyadipic acid. Indirect measuring includes measuring of a signal obtained from a secondary component, i.e., a component not being D2HG or (D)-2-hydroxyadipic acid itself, or a biological readout system, e.g., measurable cellular responses, ligands, labels, or enzymatic reaction products.

The term "amount" as used herein encompasses the absolute amount of D2HG or (D)-2-hydroxyadipic acid referred to herein, the relative amount or concentration of the D2HG or (D)-2-hydroxyadipic acid as well as any value or parameter which correlates thereto. Such values or parameters comprise intensity signal values from all specific physical or chemical properties obtained from the D2HG or (D)-2-hydroxyadipic acid by direct measurements, e.g., intensity values in mass spectra or NMR spectra. Moreover, encompassed are all values or parameters which are obtained by indirect measurements specified elsewhere in this description, e.g., biological readout systems in response to D2HG or (D)-2-hydroxyadipic acid or intensity signals obtained from specifically bound ligands. It is to be understood that values correlating to the aforementioned amounts or parameters can also be obtained by all standard mathematical operations.

The term "contacting" or "incubating" as used herein refers to bringing at least two different compounds in physical proximity as to allow physical and/or chemical interaction of said compounds. In the methods of the invention, the reaction mixture as referred to herein is contacted with a sample suspected to comprise D2HG or (D)-2-hydroxyadipic acid. A sample which can be used to this end is defined elsewhere herein. The reaction mixture shall be contacted for a time and under conditions sufficient to allow the detection of D2HG or (D)-2-hydroxyadipic acid comprised by the sample. "Contacting" as used herein may occur also in a host cell comprising or containing D2HG or (D)-2-hydroxyadipic acid. The host cell can be, for example, a bacterial cell (e.g. *E. coli*), a fungal cell, a plant cell or a mammalian host cell (e.g. human host cell). The said time and conditions will depend on the amount of D2HG or (D)-2-hydroxyadipic acid comprised by the sample. The person skilled in the art is well aware of which conditions need to be applied dependent on the host cell, kind of sample and so on. In further aspects, "contacting" occurs in a cell-free system comprising D2HG or (D)-2-hydroxyadipic acid. The cell-free system shall allow for measuring D2HG or (D)-2-hydroxyadipic acid upon contacting it with the reaction mixture referred to herein. Preferably, the methods of the invention are carried out in vitro.

The term "reaction mixture" as used herein comprises a solvent which can be, for example, water or a buffer as defined herein. It further comprises a dye as defined herein having an oxidized state and a reduced state wherein the reduced state can be distinguished from the oxidized state and wherein the dye is initially present in the oxidized state. The reaction mixture further comprises an electron transfer agent, a (D)-2-hydroxyglutarate dehydrogenase enzyme and an appropriate co-factor, as defined herein.

The term "solvent" as used herein means preferably a buffer, for example, Tris-HCl buffer (Tris buffer), $K^+$-phosphate buffer, HEPES buffer, MOPS buffer or TES buffer, pH 7.4 to 8.0. Preferably, the buffer is 0.1 M HEPES, pH 8.0.

The term "dye" as used herein means preferably resazurin or a tetrazolium salt, such as XTT, INT, MTT, MTS, TTC, CTC, NBT, WST-1, WST-3, or WST-5, or AmplexRed or AmplexRed Ultra.

The term "electron transfer agent" preferably refers to a diaphorase, PMS, Meldola blue (8-dimethylamino-2,3-benzophenoxazine hemi(zinc chloride) salt), DPIP (2,6-dichlorphen-olindophenol), or MPMS (1-methoxy-PMS).

The term "(D)-2-hydroxyglutarate dehydrogenase" (EC 1.1.99.6) as used herein is an enzyme that catalyzes, inter alia, the chemical reaction:

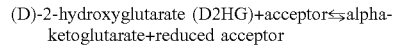

(D)-2-hydroxyglutarate (D2HG)+acceptor⇌alpha-ketoglutarate+reduced acceptor

Thus, the two substrates of this enzyme are (D)-2-hydroxyglutarate and acceptor, whereas its two products are alpha-ketoglutarate and reduced acceptor; see also FIG. 1A. Another chemical reaction catalyzed by this enzyme is shown in FIG. 1B. Acceptors or co-factors can be, for example, NAD+ or NADP+ or FAD. Enzymes with specificity to (D)-2-hydroxyglutarate exist in mammals (Achouri et al., 2004, Biochem. J. 381: 35-42), plants (Engqvist et al., 2009, J. Biol. Chem. 284 (37): 25026-37) and bacteria (Buckel, 1980, Eur. J. Biochem., 106: 439-447; Sponholz et al., 1981, Zeitschrift für Lebensmittel-Untersuchung und -Forschung, 172: 264-268). (D)-2-hydroxyglutarate dehydrogenases which are preferred for the means and methods of the invention are shown in FIG. 10. (D)-2-hydroxyglutarate dehydrogenase can be used, for example, in amounts from 0.01 to 0.25 microgram, for the detection of D2HG, in the methods of the invention. Preferably, 0.1 microgram of (D)-2-hydroxyglutarate dehydrogenase per microtiter plate well are used in the methods of the invention for determining D2HG; see also the following Examples. For the assay of the invention to estimate (D)-2-hydroxyadipic acid, a higher concentration of (D)-2-hydroxyglutarate dehydrogenase is required, e.g. 1 to 10 microgram/well, preferably 4 microgram/well; see FIG. 11 and Example 2. (D)-2-hydroxyglutarate dehydrogenase as used herein comprises native or recombinant enzyme and also encompasses variants of the aforementioned (D)-2-hydroxyglutarate dehydrogenases. Such variants have at least the same essential biological and immunological properties as the (D)-2-hydroxyglutarate dehydrogenase. In particular, they share the same essential biological and immunological properties if they are detectable by the same specific assays referred to in this specification, e.g., by ELISA assays using polyclonal or monoclonal antibodies specifically recognizing the (D)-2-hydroxyglutarate dehydrogenase. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 75%, 80%, 85%, 90%, 91%, 92%, 93%, 94%, 95%, 96%, 97%, 98%, or 99% identical to the amino sequence of the (D)-2-hydroxyglutarate dehydrogenase, preferably the (D)-2-hydroxyglutarate dehydrogenase of *Acidaminococcus fermentans* (Buckel, 1980, Eur. J. Biochem., 106: 439-447). The degree of identity between two amino acid sequences can be determined, in principle, by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Preferably, the sequence identity is over the entire length of the compared/aligned sequences. Optimal alignment of sequences for comparison may be conducted by the local homology algorithm of Smith and Waterman, 1981, Add. APL. Math. 2: 482, by the homology alignment algorithm of Needleman and Wunsch, 1970, J. Mol. Biol. 48: 443, by the search for similarity method of Pearson and Lipman, 1988, Proc. Natl. Acad Sci. (USA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of the (D)-2-hydroxyglutarate dehydrogenase, or the aforementioned types of variants as long as these fragments have the essential immunological and/or biological properties as referred to above. Such fragments may be, e.g., degradation products of the (D)-2-hydroxyglutarate dehydrogenase. Preferably, said fragment is at least 50, 60, 70, 80, 90, 100, 150, 200 or 300 amino acid residues in length and has (D)-2-hydroxyglutarate dehydrogenase activity. Further included are variants which differ due to posttranslational modifications such as phosphorylation or myristylation. Preferably, (D)-2-hydroxyglutarate dehydrogenase as used herein also encompasses the precursor proteins of (D)-2-hydroxyglutarate dehydrogenase. Preferably, the (D)-2-hydroxyglutarate dehydrogenases referred to herein are prokaryotic or mammalian (D)-2-hydroxyglutarate dehydrogenases. The amino acid sequence of the human (D)-2-hydroxyglutarate dehydrogenase is depicted in Accession no. Q8N465 (version 87). The activity of the human (D)-2-hydroxyglutarate dehydrogenase enzyme has been assayed by Wickenhagen and co-workers (J. Inherit. Metab. Dis., 2009, 32: 264-8). More preferably, the (D)-2-hydroxyglutarate dehydrogenase enzyme is or is derived from *Acidaminococcus fermentans* (Buckel, 1980, Eur. J. Biochem., 106: 439-447; Sponholz et al., 1981, Zeitschrift für Lebensmittel-Untersuchung und -Forschung, 172: 264-268; Martins et al., FEBS J. 2005 January; 272(1): 269-81). The term "(D)-2-hydroxyglutarate dehydrogenase enzyme is from *Acidaminococcus fermentans*" means that the (D)-2-hydroxyglutarate dehydrogenase enzyme comprises or consists of the amino acid sequence from the *Acidaminococcus fermentans* (D)-2-hydroxyglutarate dehydrogenase enzyme. The corresponding amino acid sequence of the (D)-2-hydroxyglutarate dehydrogenase from *Acidaminococcus fermentans* is shown, for example, in Martins et al., FEBS J. 2005 January; 272(1): 269-81 (see FIG. 1) and in accession number 1XDW_A (Version 1XDW_A GI: 62738423; 10.10.2012). This publication provides also the amino acid sequences of other members of the (D)-2-hydroxyglutarate dehydrogenase protein family which are incorporated herein by reference. "Derived from" means, for example, that said enzyme or the gene encoding for said enzyme has originally been isolated from *Acidaminococcus fermentans* and then the corresponding nucleic acid or amino acid sequence has been further modified, e.g. optimized, by recombinant methods known in the art. Such methods can be, for instance, site-specific mutations in order to improve the enzymatic activity and the like. Encompassed are also variants of the (D)-2-hydroxyglutarate dehydrogenase from *Acidaminococcus fermentans* as defined herein. Variants also encompass polynucleotides comprising a nucleic acid sequence which is capable of hybridizing to the specific nucleic acid sequences encoding the (D)-2-hydroxyglutarate dehydrogenase, preferably from *Acidaminococcus fermentans*, preferably under stringent conditions. These stringent conditions are known to the skilled worker and can be found, e.g., in Current Protocols in Molecular Biology, John Wiley & Sons, N.Y., 1989, 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., 1989, "Molecular Cloning", Cold Spring Harbor Laboratory; Hames and Higgins (Ed.), 1985, "Nucleic Acids Hybridization: A Practical Approach", IRL Press at Oxford University Press, Oxford; Brown (Ed.), 1991, "Essential Molecular Biology: A Practical Approach", IRL Press at Oxford University Press, Oxford. As evident to those skilled in the art, (D)-2-hydroxyglutarate dehydrogenase enzymes derived from different organisms or other enzymes using D2HG as a substrate can be used in the methods of the invention as well, as long as they are able to generate a suitable readout, such as the production or conversion of NADH or NADPH. Alternatively, said enzyme can be coupled to another enzyme which is able to generate such a read out.

The co-factor is preferably $NAD^+$.

The sample is preferably a tissue biopsy or tissue section, cell or cell lysate, supernatant of cultured cells, blood sample, serum sample, plasma sample, or urine sample. The sample can also be a frozen cell or tissue or paraffin embedded cell or tissue. In some preferred embodiments of the methods of the invention, the sample is from a human patient suffering from a tumor or tumorous disease or another disease or disorder as defined elsewhere herein.

However, in specific embodiments of the methods of the invention, it is envisaged that the sample is a cell-free sample.

Preferably, the sample is deproteinized if it contains proteins, prior to the methods of the invention. Deproteinization can be achieved, for example, by incubation of the protein-containing sample with proteinase K over night at 37° C. Thereafter, the degraded proteins can be precipitated with perchloric acid. Subsequently, the sample can be analyzed for the presence of D2HG in the methods of the invention.

Accordingly, in a preferred embodiment of the invention, the sample is deproteinized by (i) incubation with proteinase K over night at 37° C. and (ii) protein precipitation with perchloric acid, prior to step a) of said methods of the invention.

The methods of the invention for determining the presence and/or amount of D2HG or (D)-2-hydroxyadipic acid rely upon the conversion of a dye from one state to another. For example, in a typical format, prior to the reaction the dye absorbs at a first wavelength of radiation. The dye is then converted to a product that absorbs at a second (and different) wavelength of light. By monitoring the conversion of the dye from one state to the other, the presence and/or amount of D2HG or (D)-2-hydroxyadipic acid can be determined. A number of suitable dyes for this purpose are known in the art. The most frequently used of these indicators are electron-acceptor dyes such as tetrazolium salts. Tetrazolium salts are known in the prior art and include, for instance, MTT (3-(4,5-dimethylthiazol-2-yl)-2,5-diphenyltetrazolium bromide), XTT (sodium 3'-{(1-phenylaminocarbonyl)-3,4-tetrazolium}-bis(4-methoxy-6-nitro)benzenesulfonic acid hydrate), and MTS (3-(4,5-dimethylthiazol-2-yl)-5-(3-carboxymethoxyphenyl)-2-(4-sulphopheny-1)-2H-tetrazolium, inner salt).

A typical assay using the tetrazolium salt MTS for the analysis of cell viability and proliferation has been described by Buttke et al., 1993, J. Immunol. Methods, 157: 233-240). Dunigan and co-workers (1995, BioTechniques, 19: 640-649) proceed to describe that one of the hallmarks of metabolism is the generation of energy via complex redox reactions of organic molecules. A great number of these reactions utilize beta-nicotinamide adenine dinucleotide (NADH) or beta-nicotinamide adenine dinucleotide phosphate (NADPH) as hydrogen donors. While it is theoretically possible to monitor NADH and NADPH concentrations directly via spectrophotometry, from a practical standpoint, direct spectrophotometric analysis is limited due to the presence of numerous components that absorb light near the absorption maximum of NADH and NADPH (epsilon=16,900 at lambda max. of 259 nm). For example, NAD+, NADP+, DNA, RNA, and most proteins have absorption maxima at approximately 260 nm.

In one preferred embodiment of the methods of the invention, the tetrazolium salt XTT is being used in a XTT/formazan assay as shown, e.g., in FIG. 1C. This assay uses a coupled two-step reaction: In the first step, (D)-2-hydroxyglutarate dehydrogenase catalyzes the reduction of NAD+ to NADH and H+ by oxidation of (D)-2-hydroxyglutarate to alpha-ketoglutarate (FIG. 1A). Alternatively, (D)-2-hydroxyglutarate dehydrogenase catalyzes the reduction of NAD+ to NADH and H+ by oxidation of (D)-2-hydroxyadipic acid to alpha-ketoadipic acid (FIG. 1B). In the second step of the reaction, XTT (2,3-bis(2-methoxy-4-nitro-5-sulfo phenyl)-2H-tetrazolium-5-carboxyanilite disodium salt) is reduced with the help of the electron transfer agent N-methyl dibenzopyrazine methyl sulfate (PMS) to highly colored formazan which absorbs strongly at about 490 to 520 nm. Colorimetric detection of formazan according to the method of the invention is preferably carried out at 450 nm.

Tetrazolium salts have been widely used as detection reagents for many years in histochemical localization studies and cell biology assays (Altman, 1976, Prog. Histochem. Cytochem. 9: 1-56, Berridge et al., 2005, Biotechnology Annual Review 11: 127-152). The second generation tetrazolium dye, XTT (sodium 2,3,-bis(2-methoxy-4-nitro-5-sulfophenyl)-5-[(phenylamino)-carbonyl]-2H-tetrazolium inner salt), can be effectively used in cell-based assays to measure cell growth, cytotoxicity, and apoptosis (Berridge et al., loc. cit.; Scudiero et al., 1988, Cancer Res. 48: 4827-4833; Marshall et al., 1999, Growth Regulation 5: 69-84). XTT is reduced to a soluble, brightly colored orange derivative by a mix of cellular effectors. The sensitivity of an XTT assay is greatly improved by the usage of an intermediate electron carrier, PMS (N-methyl dibenzopyrazine methyl sulfate). PMS helps drive XTT reduction and the formation of its formazan derivative.

The XTT cell proliferation assay was first described in 1988 by Scudiero et al. (loc. cit.) as an effective method to measure cell growth and drug sensitivity in tumor cell lines. XTT is a colorless or slightly yellow compound that when reduced becomes brightly orange. This color change is accomplished by breaking apart the positively-charged quaternary tetrazole ring (Berridge, loc. cit.). The formazan product of XTT reduction is soluble and can be used in real-time assays.

XTT is thought to be excluded from entering cells by its net negative charge (Berridge, loc. cit.). Considerable evidence suggests that XTT dye reduction occurs at the cell surface facilitated by trans-plasma membrane electron transport. Mitochondrial oxidoreductases are thought to contribute substantially to the XTT response with their reductants being transferred to the plasma membrane. It has been proposed that XTT assays actually measure the pyridine nucleotide redox status of cells (Berridge, loc. cit., Marshall, loc. cit.).

Though XTT can be used alone as a detection reaction, the results are, however, not optimal. XTT assay results are greatly improved when an intermediate electron acceptor, such as PMS (N-methyl dibenzopyrazine methyl sulfate), is used with XTT. Findings suggest that PMS mediates XTT reduction by picking up electrons at the cell surface, or at a site in the plasma membrane that is readily accessible, and forms a reactive intermediate that then reduces XTT to its highly pigmented formazan product.

In another preferred embodiment of the methods of the invention, the methods use a resazurin/diaphorase assay as shown, e.g., in FIG. 1D. This assay uses a coupled two-step reaction, too: In the first step, the 2-hydroxyglutarate dehydrogenase catalyzes the reduction of $NAD^+$ to NADH and $H^+$ by oxidation of (D)-2-hydroxyglutarate to alpha-ketoglutarate (FIG. 1A). Alternatively, (D)-2-hydroxyglutarate dehydrogenase catalyzes the reduction of NAD+ to NADH and H+ by oxidation of (D)-2-hydroxyadipic acid to alpha-ketoadipic acid (FIG. 1B). In the second step of the reaction, diaphorase uses the newly-formed NADH and $H^+$ to catalyze the reduction of resazurin to the fluorescent resorufin.

The oxidation of (D)-2-hydroxyglutarate to alpha-ketoglutarate or the oxidation of (D)-2-hydroxyadipic acid to alpha-ketoadipic acid result in the production of NADH. In a second reaction, the dye resazurin is reduced in a reaction powered by the NADH produced in the first reaction and catalyzed by the electron transfer agent diaphorase. The preferred electron transfer agent diaphorase catalyzes the reduction of resazurin to resorufin, a reduction powered by NADH.

The end result is a method wherein the amount of D2HG or (D)-2-hydroxyadipic acid is measured indirectly by measuring the reduction of a dye, that reduction being driven via a reaction that is linked to the oxidation of a substrate (e.g., the (D)-2-hydroxyglutarate to alpha-ketoglutarate conversion or the (D)-2-hydroxyadipic acid to alpha-ketoadipic acid conversion, by the (D)-2-hydroxyglutarate dehydrogenase). The amount of the reduced dye formed is proportional to the amount of D2HG or (D)-2-hydroxyadipic acid in the tested sample. The production of the reduced form of the dye can be measured calorimetrically or fluorimetrically, or by other electromagnetic spectral measuring device, depending upon the dye. Resorufin can be measured either colorimetrically or fluorimetrically. Suitable measuring devices are exceedingly well known in the art and can be purchased from a host of commercial suppliers.

In particular, when the dye used is resazurin, reduction can be detected either by absorbance colorimetry or by fluorimetry. Resazurin is deeply blue in color and is essentially non-fluorescent, depending upon its level of purity. Resorufin, the reduced form of resazurin, is red and very fluorescent. When using colorimetry, the reaction is monitored at wavelengths well known in the art to be an absorption maximum for resorufin (approximately 570 nm). Fluorescence measurements of resorufin are made by exciting at wavelengths well known in the art (approximately 530 to 560 nm) and measuring the emission spectrum (known to the art to have a maximum at about 590 nm). Because fluorometric detection is more sensitive than spectrophotometric detection, in the preferred embodiment of the methods of the invention, resazurin is used as the dye and the production of resorufin is detected fluorimetrically. Preferably, excision is carried out at 540 plus/minus 10 nm and emission is detected at 600 plus/minus 10 nm, in this assay.

The methods described herein are inherently quantitative in that the amount of the reduced form of the dye produced is proportional to the amount of D2HG or (D)-2-hydroxyadipic acid in the analyzed sample. The methods of the invention can also be used for qualitative analyses, for example, for detecting D2HG in sections of solid tumors. The measurement of D2HG differs dependent on the choice of assay used for the NADH determination. Using the PMS/XTT assay, the measured values are preferably determined every two minutes over 20 minutes. Then the slope of the line is determined to calculate the concentration of D2HG. Using the diaphorase/resazurin system, the end point is preferably measured which allows the immediate calculation of the amount of D2HG in the tested sample.

In an even more preferred embodiment of the methods of the invention, the reduced state of the dye in the methods of the invention is being caused by the oxidation of (D)-2-hydroxyglutarate to alpha-ketoglutarate or the oxidation of (D)-2-hydroxyadipic acid to alpha-ketoadipic acid, catalyzed by a (D)-2-hydroxyglutarate dehydrogenase enzyme. The utilized assay is preferably the resazurin/diaphorase assay using NAD+ as cofactor. The production of the reduced state of the dye as referred to herein is preferably measured via fluorescent spectroscopy. The benefits of said assay are evident from the following examples.

In another preferred embodiment of the methods of the invention, the methods use a luciferase assay, as shown, e.g., in FIG. 1E. In principle, the assay with luciferase read-out works the same way as the diaphorase/resazurin read-out. Instead of resazurin, bacterial luciferase, FMN and a long chain aldehyde are added to the reaction mixture.

After an incubation time (of about 10-20 minutes), the luminescence is measured in a plate reader. Luciferase assays have been described in the art (Vaughan & Mopper, 1990, Analytica Chimica Acta 231: 299-303; Wienhausen & De Luca, 1982, Analytical Biochemistry 127: 380-388).

Preferably, the luciferase is a bacterial luciferase. Bacterial luciferase (LU) (I.U.B.: 1.14.14.3) catalyzes the oxidation of reduced flavin mononucleotide ($FMNH_2$) and a long chain aldehyde by molecular oxygen to yield FMN, the corresponding acid, $H_2O$ and light (Baldwin et al., 1975; Balny and Hastings, 1975; Becvar and Hastings, 1975).

$$FMNH_2 + RCHO + O_2 \rightarrow FMN + RCO_2H + H_2O + \text{light}$$

See also the publication by Hastings et al., 1966, in this respect. The aldehyde is not essential to the reaction but has a striking effect upon the luminescence. The FMN can be reduced by molecular hydrogen with Pt or Pd catalyst, or by treatment with dithionite, but because $FMNH_2$ is so rapidly oxidized by air, the use of NADH is a more workable laboratory method and more useful in analytical applications. The mechanism by which bacterial luciferase functions to produce light was studied by Dr. J. Woodland Hastings' group. In an article describing partial and rapid purification of LU using affinity chromatography, Waters et al. (1974) describe the specific activity of highly purified luciferase as being $1.4 \times 10^{14}$ quanta per second per milligram. Brolin et al., 1971, developed a very sensitive assay for trace metabolic intermediates which can be involved in pyridine nucleotide dependent dehydrogenase reactions using bacterial luciferase. See also Chappelle and Picciolo, 1971, for its use in assaying FMN and FAD. See Aflalo and DeLuca, 1987, for its use monitoring ATP. A review of the use of firefly luciferase as a tool in molecular and cell biology is offered by Gould and Subramani, 1988. A review of clinical applications for the enzyme is given by Kricka, 1988.

The assays and methods provided by the present invention are advantageous for the following reasons: They are homogenous assay which are easy to use with no solubilization step required. They are suitable for high-throughput analysis and reveal fast results. In addition, they are automation-friendly. The assays are highly sensitive and allow detection of very low amounts of D2HG or (D)-2-hydroxyadipic acid. This holds particularly true for the resazurin/diaphorase assay, as shown in the following examples. Last but not least, said assays and methods are characterized by reproducible accuracy: The dye absorbance is proportional to the amount of D2HG or (D)-2-hydroxyadipic acid in the tested sample. In sum, rapid, inexpensive and sensitive enzymatic assays for the detection of D2HG or (D)-2-hydroxyadipic acid are provided by the present invention. For example, the quantification limit of the enzymatic assay for D2HG in tumor tissue is 0.44 micromolar and in serum 2.77 micromolar.

The invention further relates to a kit comprising the reagent mixture referred to herein. Preferably, the kit comprises (i) a solvent (preferably a buffer, such as Tris buffer, pH 8.0), (ii) a dye (preferably resazurin or a tetrazolium salt such as XTT) having an oxidized state and a reduced state wherein the reduced state can be distinguished from the oxidized state, and wherein the dye is initially present in the oxidized state, (iii) an electron transfer agent (preferably diaphorase or PMS or Meldola blue), (iv) a 2-hydroxyglutarate dehydrogenase enzyme, and (v) an appropriate co-factor (preferably $NAD^+$ or $NADP^+$). Preferably, the kit is for the determination of the presence and/or amount of D2HG or (D)-2-hydroxyadipic acid in a sample as defined elsewhere herein. More preferably, the kit is for determination of the presence and/or amount of D2HG in a sample of a subject suffering from a disease or disorder as defined elsewhere herein. It is further preferred that the 2-hydroxyglutarate dehydrogenase enzyme is or is derived from *Acidaminococcus fermentans*.

The definitions and embodiments of the methods of the invention apply mutatis mutandis to the kit of the invention.

The term "kit" as used herein refers to a collection of the aforementioned means, preferably, provided in separate form within a single container. The container, also preferably, comprises instructions for carrying out the methods of the present invention. The invention, thus, relates to a kit comprising said reaction mixture for measuring the amount of D2HG or (D)-2-hydroxyadipic acid referred to herein. Examples for such reaction mixtures as well as methods for their use have been given in this specification. The kit, preferably, contains the aforementioned reagent mixture in a ready-to-use manner. Further, the kit can comprise means and agents for the establishment of D2HG or (D)-2-hydroxyadipic acid standard curves, e.g. pre-determined amounts of D2HG or (D)-2-hydroxyadipic acid, as shown in the following examples. Preferably, the kit may additionally comprise instructions, e.g., a user's manual for establishing D2HG or (D)-2-hydroxyadipic acid standard curves and interpreting the results of any determination(s) with respect to the diagnoses provided by the methods of the present invention. Particularly, such manual may include information for allocating the amounts of the determined D2HG to the kind of diagnosis. Details are to be found elsewhere in this specification. Additionally, such user's manual may provide instructions about correctly using the components of the kit for determining the amount(s) of D2HG or (D)-2-hydroxyadipic acid. A user's manual may be provided in paper or electronic form, e.g., stored on CD or CD ROM. The present invention also relates to the use of said kit in any of the methods according to the present invention.

Said kit is advantageous since it is non-radioactive and thus safe, without any hazardous waste. In addition, the kit is stable for 18 months when stored under refrigeration in the dark and thus convenient to store.

All references cited in this specification are herewith incorporated by reference with respect to their entire disclosure content and the disclosure content specifically mentioned in this specification.

The Figures show:

FIG. 1:

(A) Reaction scheme of the (D)-2-hydroxyglutarate dehydrogenase (D2HG dehydrogenase). (D)-2-hydroxyglutarate dehydrogenase catalyzes the reduction of NAD+ to NADH and H+ by oxidation of (D)-2-hydroxyglutarate to alpha-ketoglutarate.

(B) Reaction scheme of the (D)-2-hydroxyglutarate dehydrogenase (D2HG dehydrogenase). The (D)-2-hydroxyglutarate dehydrogenase catalyzes also the reduction of NAD+ to NADH and H+ by oxidation of (D)-2-hydroxyadipic acid to alpha-ketoadipic acid.

(C) shows the NADH-detection reaction using the PMS/XTT assay in which the produced formazan was detected via the measurement of absorption at 450 nm.

(D) depicts the NADH-detection reaction using the diaphorase/resazurin assay in which the produced resorufin was detected via fluorescence measurement, with excitation at 540 nm and emission at 600 nm.

(E) shows the NADH-detection reaction via two additional enzymes, diaphorase and bacterial luciferase, and in the presence of oxygen, flavin mononucleotide (FMN) and a long-chain aldehyde. Read-out is the produced light of the last coupled reaction.

FIG. 2:

Flow chart of the determination of (D)-2-hydroxyglutarate (D2HG).

(A) Samples comprising proteins were deproteinized by incubation with proteinase K over night at 37° C. and subsequent precipitation by perchloric acid. Samples and standard curves were carried out as triplicate.

(B) The measurement of D2HG differs dependent on the choice of assay used for the NADH determination: In the shown table, possible assay read-outs are listed and described in detail. (i) Absorbance measurement using the PMS/tetrazolium, (ii) fluorescence measurement with diaphorase/resazurin, and (iii) luminescence measurement with diaphorase/luciferase.

FIG. 3:

Reagents and concentrations used for the PMS/XTT assay and diaphorase/resazurin assay, respectively, for the measurement of D2HG.

FIG. 4:

Concentrations of D2HG used for the preparation of the D2HG standard curve.

FIG. 5:

D2HG standard curves resolved in water, serum and plasma and determined using the PMS/XTT assay. Applied is the slope against the concentration of D2HG (0 to 500 µM).

FIG. 6:

D2HG standard curve resolved in water measured using the diaphorase/resazurin assay (in triplicate).

FIG. 7:

Extract of the D2HG standard curve (0 to 1250 pmol D2HG corresponds to 0 to 50 µM resolved in water measured by the diaphorase/resazurin assay (in triplicate).

Figure 2:
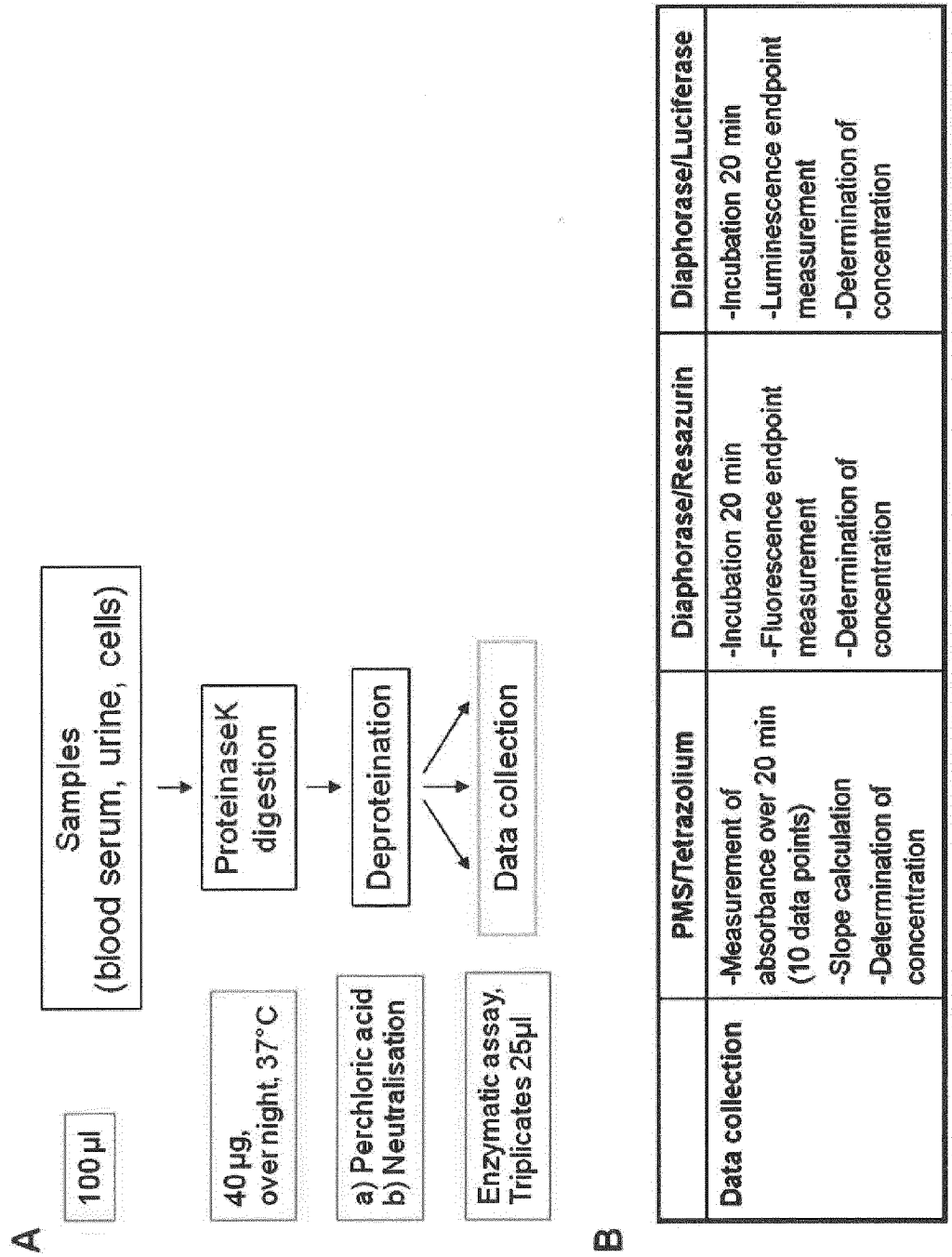

FIG. 8:

D2HG was diluted in water, blood serum, and urine to get a standard curve (0-375 pmol=0-15 µM). Samples were prepared according to the protocol in FIG. 2 and assayed with the diaphorase/resazurin read-out. In the graph, the relative fluorescence (RFU) is blotted against the D2HG concentration.

FIG. 9:

Measurement of sera of patients suffering from acute myeloid leukemia (AML). These patients carry an IDH1 mutation which results in the production of D2HG. Comparison between gas chromatography-mass spectrometry (GC-MS) (single determination) and enzyme assay of the invention using the diaphorase/resazurin read-out (in triplicate). In comparison, sera of healthy persons who did not carry an IDH1 mutation have been tested. These samples were D2HG negative.

FIG. 10:

(D)-2-hydroxyglutarate dehydrogenases which can be used for the means and methods of the invention: Organisms, protein length and accession numbers are indicated.

FIG. 11:

Reagents and concentrations used for the diaphorase/resazurin assay, respectively, for the measurement of (D)-2-hydroxyadipic acid.

FIG. 12:

(D)-2-hydroxyadipic acid standard curve resolved in water measured using the diaphorase/resazurin assay (in duplicate).

FIG. 13:

Detection of (D)-2-hydroxyadipic acid resolved in water measured using the PMS/XTT assay (in triplicate).

The invention is now further illustrated by the following examples which, however, are not construed to limit the scope of the invention.

EXAMPLE 1

Determination of (D)-2-hydroxyglutarate

For determination of (D)-2-hydroxyglutarate, the (D)-2-hydroxyglutarate dehydrogenase of *Acidaminococcus fermentans* has been used. This enzyme has originally been described by Buckel (Buckel, 1980, Eur. J. Biochem., 106: 439-447) who has used the (D)-2-hydroxyglutarate dehydrogenase for the determination of D2HG formed enzymatically from glutaconate and in fermented drinks such as wine (Buckel, 1980, Eur. J. Biochem., 106: 439-447; Sponholz et al., 1981, Zeitschrift für Lebensmittel-Untersuchung und -Forschung, 172: 264-268). The (D)-2-hydroxyglutarate dehydrogenase catalyzes the NADH-dependent reduction of alpha-ketoglutarate to (D)-2-hydroxyglutarate (see FIG. 1A). However, said enzyme can also be utilized in the opposite direction. At neutral pH, at which the enzyme is active, the reaction equilibrium is on the side of production of D2HG. Consequently, when using said enzyme for the measurement of D2HG, the reaction reaches equilibrium after only a few percent of D2HG has been converted to α-ketoglutarate. To get complete conversion, the formed NADH is irreversibly reoxidized either by PMS/XTT or by diaphorase/resazurin resulting in the colored formazane or the fluorescent resorufin, respectively.

For determining the concentration of D2HG, two different approaches, i.e. the PMS/XTT assay and the diaphorase/resazurin assay, have been used in the methods of the invention:
  a) PMS/XTT assay
    In a coupled reaction, the tetrazolium salt XXT (2,3-bis(2-methoxy-4-nitro-5-sulfophenyl)-2H-tetrazolium-5-carboxyanilite disodium salt) is reduced in cooperation with PMS, thereby resulting in the orange colored and water-soluble formazan which can be detected at a wavelength of 450 nm (see FIG. 1C).
  b) Diaphorase/resazurin assay
    In a coupled reaction, the diaphorase uses NADH for the reduction of resazurin to the fluorescent resorufin which can be excised at 540 nm. The emission is determined at 600 nm (see FIG. 1D).

By using said assays, D2HG concentrations have been determined in water, cell lysates, blood sera and blood plasma and urine. Determination of D2HG in water does not require any processing prior to the assay. When protein-containing samples were used, the sample was first incubated with proteinase K at 37° C. over night. Thereafter, the digested proteins were precipitated by perchloric acid (see FIG. 2(A)). FIG. 3 shows reagents and corresponding concentrations used for the PMS/XTT assay and the diaphorase/resazurin assay. The assays were carried out in 96-well format with a total assay volume of 100 μl. In parallel, a standard curve with defined concentrations of D2HG has been established (see FIG. 4). The standard sample ran the same procedure as the test sample.

Figure 5:
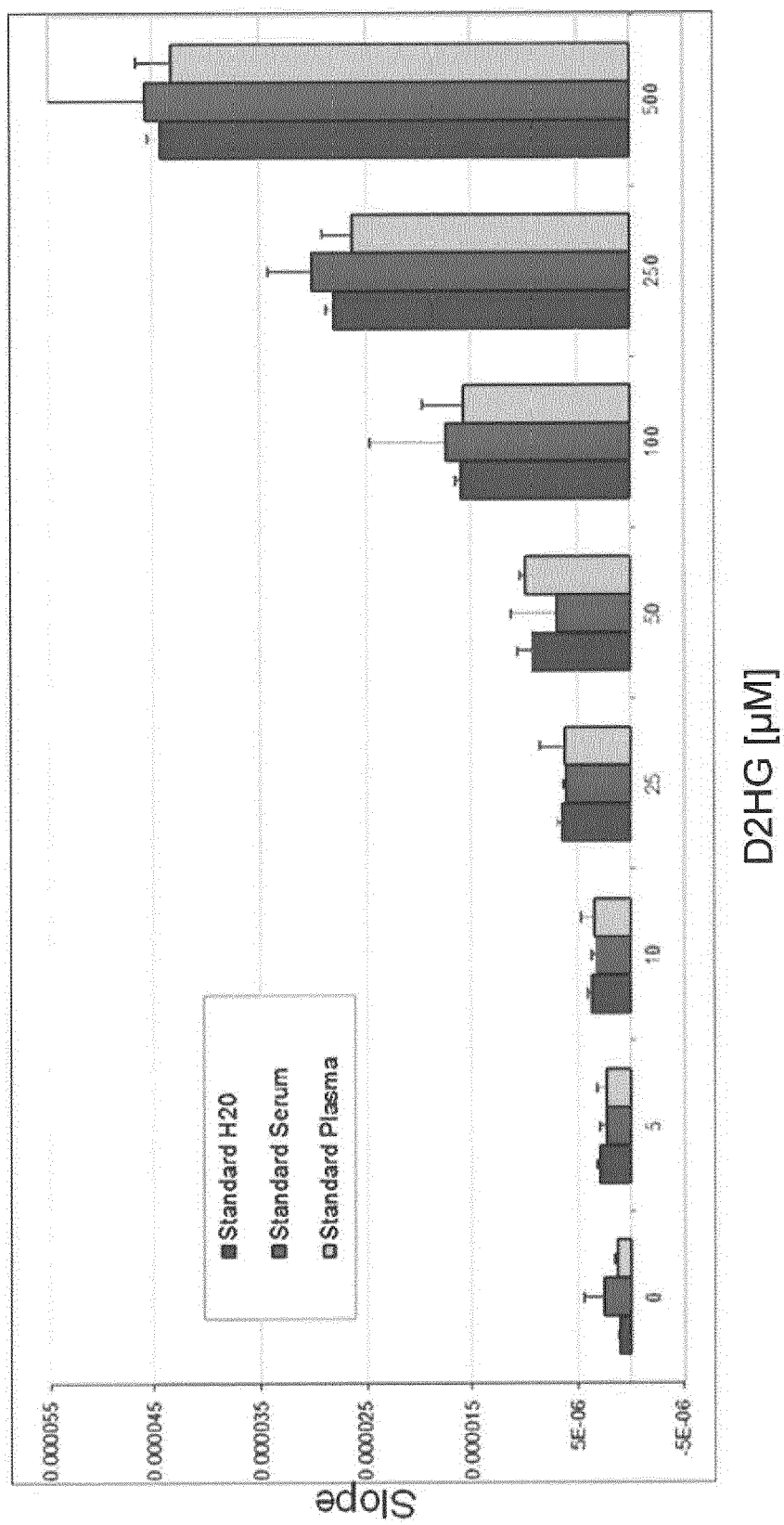

As shown in FIG. 5, D2HG can readily be determined in water, sera or plasma samples using the PMS/XTT assay. However, it has been found that in this case, a reliable sample determination is possible only in samples containing a D2HG concentration of more than 25 μM. Furthermore, the standard deviation was relatively high.

Figure 6:
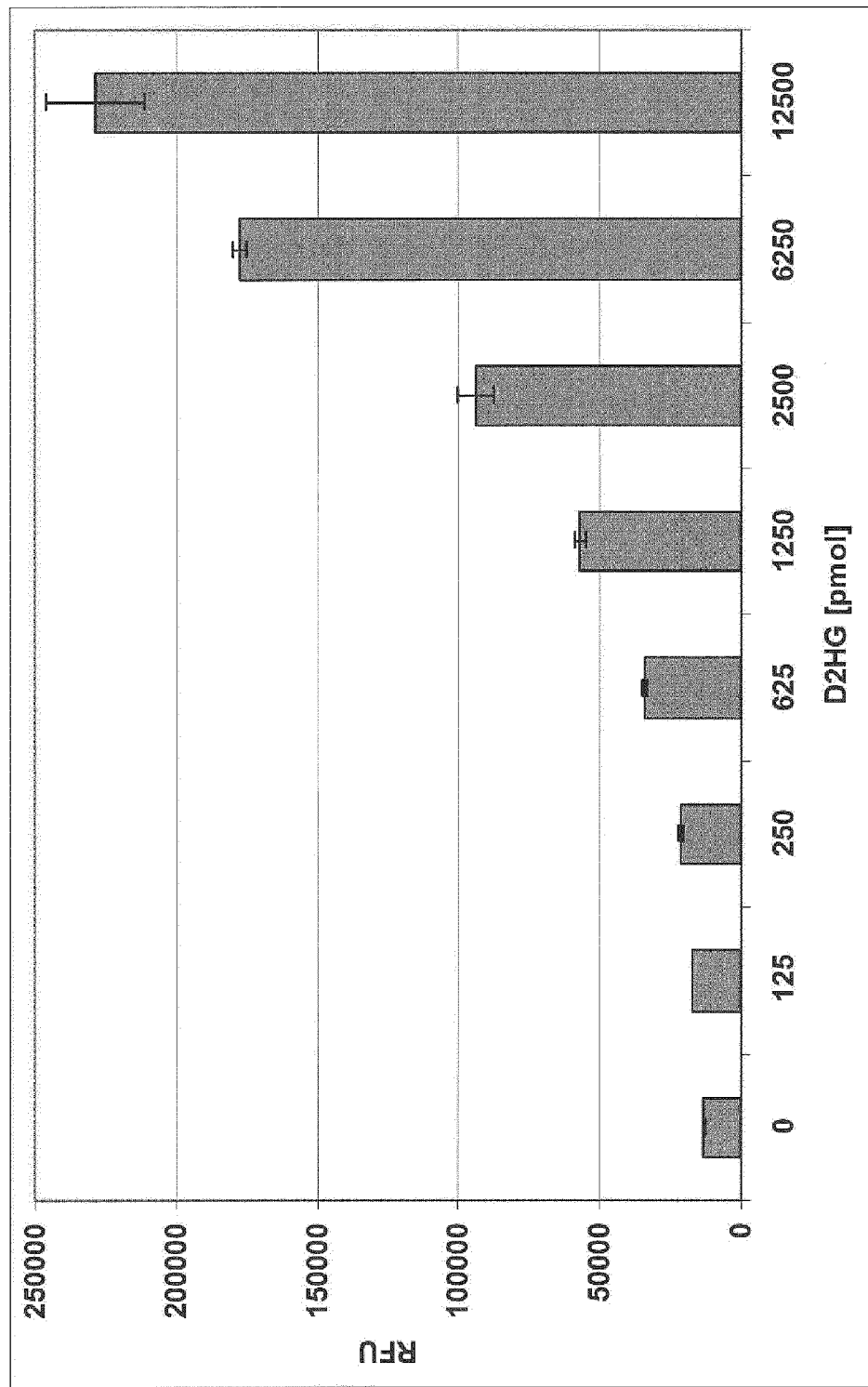
Figure 7:
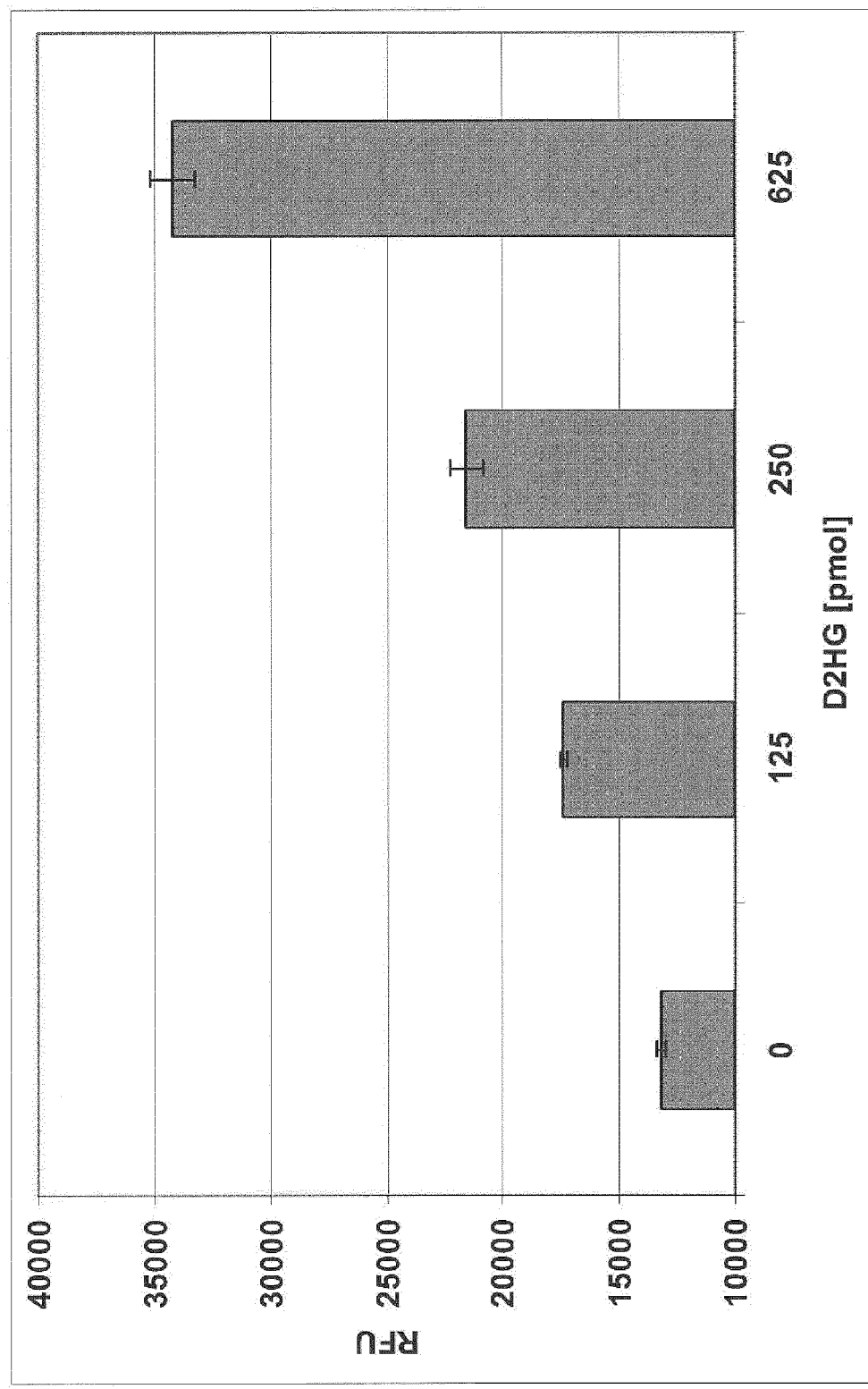

In contrast thereto, the use of the diaphorase/resazurin assay is significantly more sensitive and exact, as evident from the very small error bars and the high resolution even at low D2HG concentrations, as can be derived from FIGS. 6 and 7.

Accordingly, the diaphorase/resazurin assay offers more advantages than the PMS/XTT assay in determining the amounts of D2HG in samples.

Figure 8:
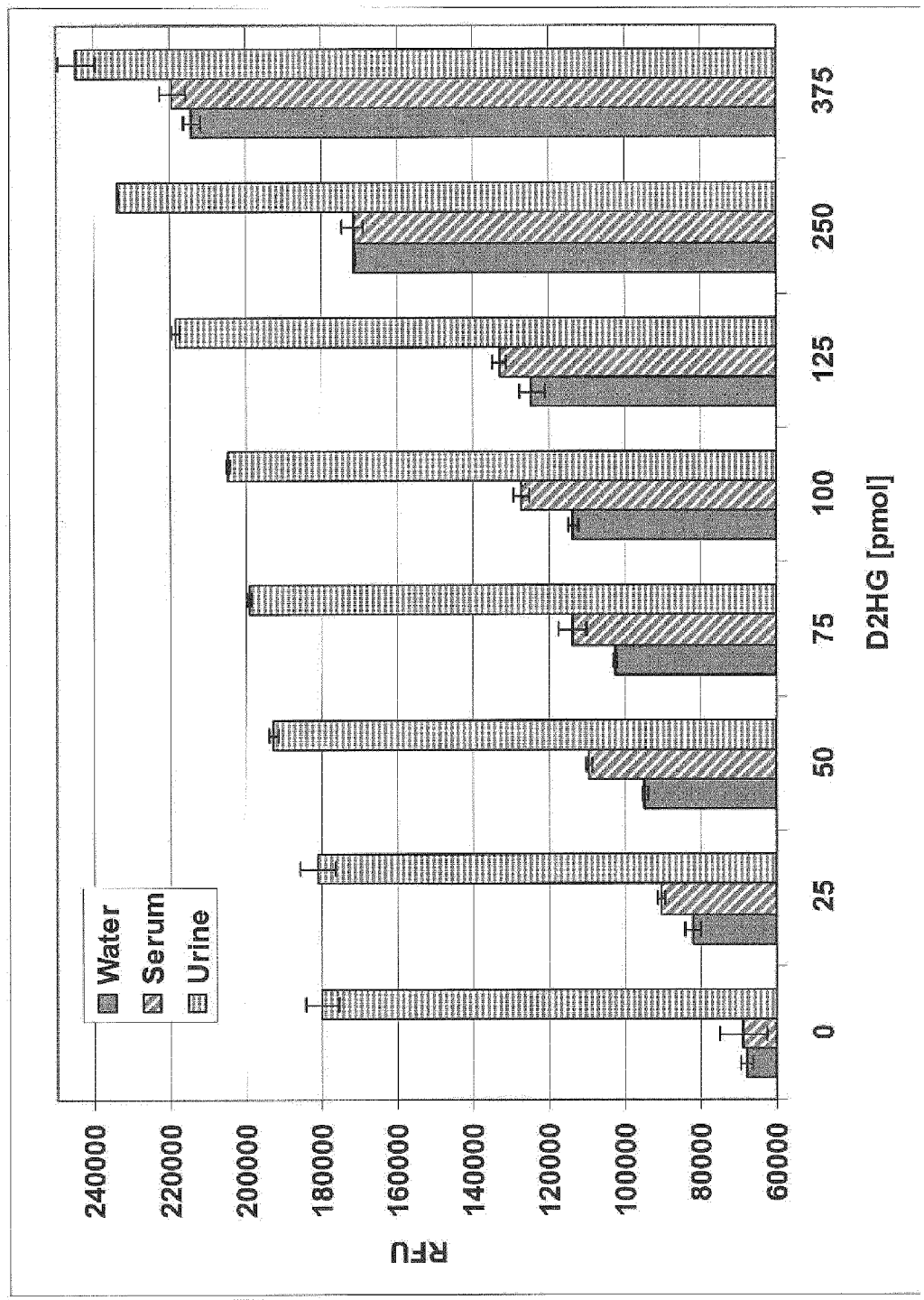

As shown in FIG. 8, D2HG was diluted in water, blood serum and urine to get a standard curve (0-375 pmol=0-15 μM). Samples were prepared according to the protocol of FIG. 2 and assayed with the diaphorase/resazurin read-out. In the graph, the relative fluorescence (RFU) is blotted against the concentration of D2HG.

Figure 9:
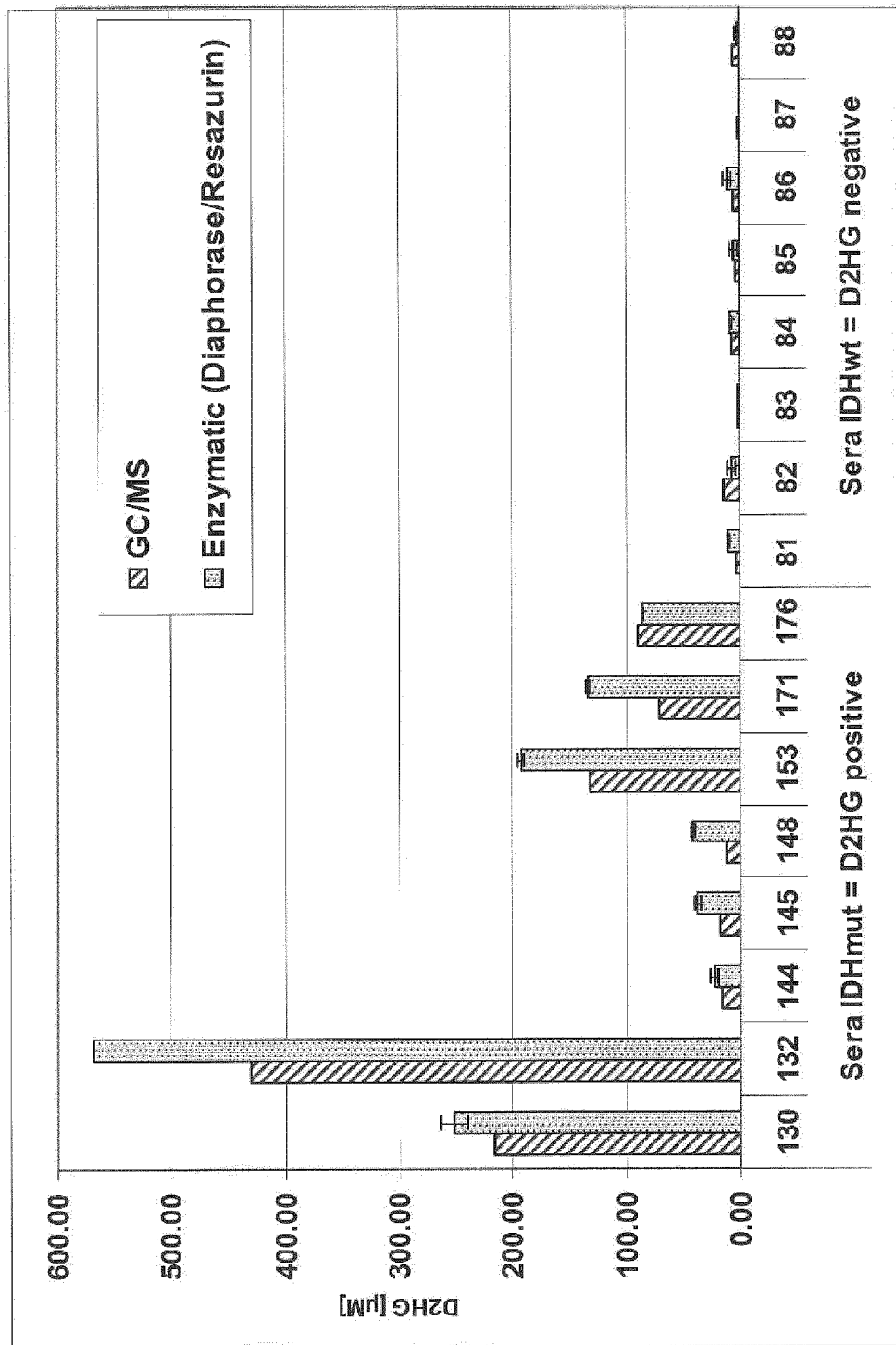

Further, D2HG has been determined in blood sera of AML patients who carry IDH1 mutations and which produce D2HG, by comparing gas chromatography-mass spectrometry (GC-MS, the method of choice in the prior art) and the diaphorase/resazurin assay of the invention; see FIG. 9. The results obtained for the GC-MS measurements and of the diaphorase/resazurin assay are comparable. In comparison, sera of healthy persons who did not carry an IDH1 mutation have been tested. These samples were D2HG negative.

EXAMPLE 2

Determination of (D)-2-hydroxyadipic acid

For determination of (D)-2-hydroxyadipic acid, again the (D)-2-hydroxyglutarate dehydrogenase of *Acidaminococcus fermentans* has been used (Buckel, loc. cit.). The (D)-2-hydroxyglutarate dehydrogenase catalyzes not only the NADH-dependent reduction of alpha-ketoglutarate to (D)-2-hydroxyglutarate (see FIG. 1A). It also catalyzes the NADH-dependent reduction of alpha-ketoadipic acid to (D)-2-hydroxyadipic acid, though with lower affinity (see FIG. 1B). However, said enzyme can also be utilized in the opposite direction. At neutral pH, at which the enzyme is active, the reaction equilibrium is on the side of production of (D)-2-hydroxyadipic acid. Consequently, when using said enzyme for the measurement of (D)-2-hydroxyadipic acid, the reaction reaches equilibrium after only a few percent of (D)-2-hydroxyadipic acid has been converted to alpha-ketoadipic acid. To get complete conversion, the formed NADH is irreversibly reoxidized either by PMS/XTT or by diaphorase/resazurin resulting in the colored formazane or the fluorescent resorufin, respectively.

For determining the concentration of (D)-2-hydroxyadipic acid, the two different approaches indicated in Example 1, i.e. the PMS/XTT assay and the diaphorase/resazurin assay, have been used.

By using said assays, (D)-2-hydroxyadipic acid concentrations have been determined in water. Determination of (D)-2-hydroxyadipic acid in water does not require any processing, prior to the assay. For the PMS/XTT assay, the same reagents and concentrations as indicated in FIG. 3 for the measurement of D2HG have been used for determining (D)-2-hydroxyadipic acid. FIG. 11 shows the reagents and corresponding concentrations used in the diaphorase/resazurin assay for determining (D)-2-hydroxyadipic acid. The only difference using these assays to estimate (D)-2-hydroxyadipic acid instead of D2HG is a higher concentration of (D)-2-hydroxyglutarate dehydrogenase (up to 4 microgram/well for the measurement of (D)-2-hydroxyadipic acid instead of 0.1 microgram/well for the measurement of D2HG). The assays were carried out in 96-well format with a total assay volume of 100 µl. In parallel, a standard curve with defined concentrations of (D)-2-hydroxyadipic acid has been established. The standard sample ran the same procedure as the test sample.

Figure 13:
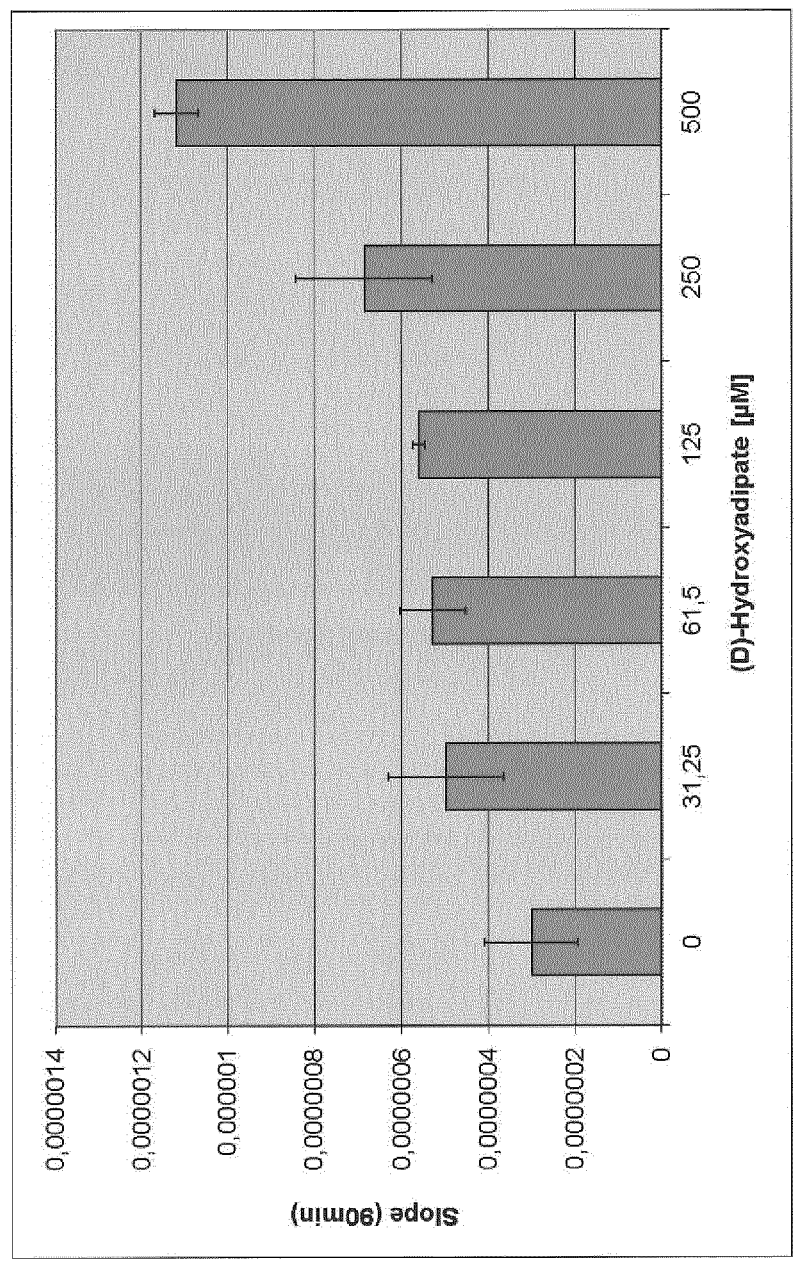

(D)-2-hydroxyadipic acid could readily be determined in water using the PMS/XTT assay; see FIG. 13. However, it has been found that in this case, a reliable sample determination is possible only in samples containing higher (D)-2-hydroxyadipic acid concentrations (more than 100 micromolar). Furthermore, the standard deviation was relatively high.

Figure 12:
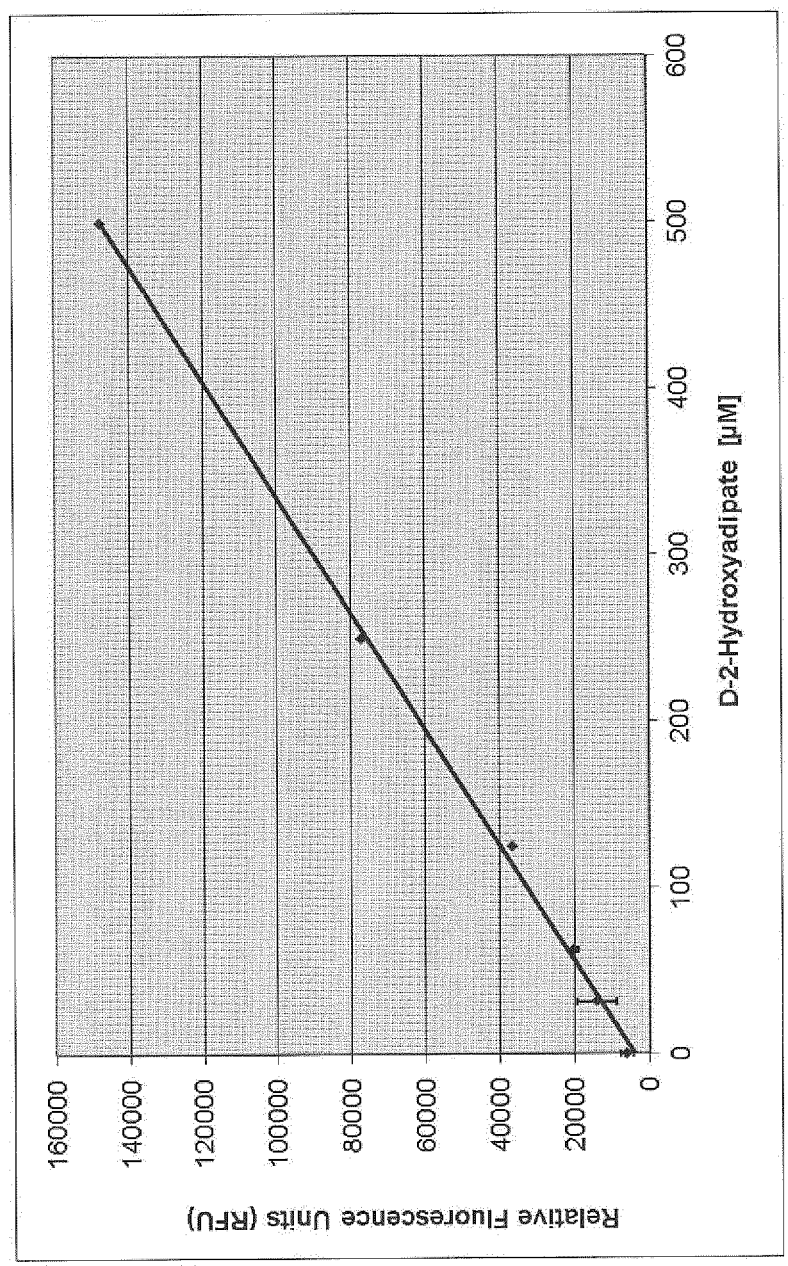

In contrast, the use of the diaphorase/resazurin assay was significantly more sensitive and exact, as evident from the very small error bars and the high resolution even at lower (D)-2-hydroxyadipic acid concentrations; see FIG. 12.

Accordingly, again, the diaphorase/resazurin assay offers more advantages than the PMS/XTT assay, in determining the amounts of (D)-2-hydroxyadipic acid in samples.

The invention claimed is:

1. A method for detecting (D)-2-hydroxyglutarate or (D)-2-hydroxyadipic acid in a sample, the method comprising:
    a) contacting a sample with a reagent mixture, wherein said reagent mixture comprises:
        (i) a solvent,
        (ii) a dye having an oxidized state and a reduced state, wherein the reduced state can be distinguished from the oxidized state and wherein the dye is initially present in the oxidized state,
        (iii) an electron transfer agent,
        (iv) a (D)-2-hydroxyglutarate dehydrogenase enzyme, and
        (v) a cofactor; and
    b) detecting (D)-2-hydroxyglutarate or (D)-2-hydroxyadipic acid by measuring the production of the reduced state of the dye.

2. The method of claim 1, wherein in step a) the reduced state of the dye can be distinguished from the oxidized state of the dye fluorometrically and wherein in step b) the production of the reduced state of the dye is measured via fluorescent spectroscopy.

3. The method of claim 1, wherein in step a) the reduced state of the dye can be distinguished from the oxidized state of the dye colorimetrically and wherein in step b) the production of the reduced state of the dye is measured via visible spectroscopy.

4. The method of claim 1, wherein in step a) the dye is resazurin or a tetrazolium salt, preferably XTT (2,3-bis-(2-methoxy-4-nitro-5-sulfophenyl)-2H-tetrazolium-5-carboxanilide, disodium salt).

5. The method of claim 1, wherein in step a) the electron transfer agent is diaphorase or PMS (N-methyl dibenzopyrazine methyl sulfate) or Meldola blue.

6. The method of claim 1, wherein in step a) the cofactor is NAD+ or NADP+.

7. The method of claim 6, wherein in step a) the enzyme is a mammalian or prokaryotic (D)-2-hydroxyglutarate dehydrogenase.

8. The method of claim 7, wherein the (D)-2-hydroxyglutarate dehydrogenase is from *Acidaminococcus fermentans*.

9. The method of claim 1, wherein the sample is a tissue, a tissue section, a biopsy, a cell, a cell lysate, a blood sample, a serum sample, a plasma sample or an urine sample.

10. A method for diagnosing and/or monitoring a (D)-2-hydroxyglutarate-associated disease in a subject, the method comprising:
    a) contacting a sample of said subject with a reagent mixture, wherein said reagent mixture comprises:
        (i) a solvent,
        (ii) a dye having an oxidized state and a reduced state, wherein the reduced state can be distinguished from the oxidized state and wherein the dye is initially present in the oxidized state,
        (iii) an electron transfer agent,
        (iv) a (D)-2-hydroxyglutarate dehydrogenase enzyme, and
        (v) a cofactor; and
    b) detecting (D)-2-hydroxyglutarate by measuring the production of the reduced state of the dye, thereby diagnosing and/or monitoring a (D)-2-hydroxyglutarate-associated disease in said subject.

11. The method of claim 10, wherein said (D)-2-hydroxyglutarate-associated disease is a tumorous disease selected from the group consisting of diffuse glioma, acute myeloid leukemia (AML), chondrosarcoma, cholangiocarcinoma and thyroid cancer; or wherein said (D)-2-hydroxyglutarate-associated is glutaric aciduria.

12. The method of claim 11, wherein said diffuse glioma is an astrocytoma WHO grade II (AII), astrocytoma WHO grade III (AIII), oligodendroglioma WHO grade II (OII), oligodendroglioma WHO grade III (OIII), oligoastrocytoma WHO grade II (OAII), oligoastrocytoma WHO grade III (OAIII), or secondary glioblastoma.

13. A method for diagnosing a mutation in an isocitrate dehydrogenase (IDH) gene or in a (D)-2-hydroxyglutarate (D2HG) dehydrogenase gene in a subject, the method comprising:
    a) contacting a sample of said subject with a reagent mixture, wherein said reagent mixture comprises:
        (i) a solvent,
        (ii) a dye having an oxidized state and a reduced state, wherein the reduced state can be distinguished from the oxidized state and wherein the dye is initially present in the oxidized state,
        (iii) an electron transfer agent,
        (iv) a (D)-2-hydroxyglutarate dehydrogenase enzyme, and
        (v) a cofactor; and
    b) detecting (D)-2-hydroxyglutarate by measuring the production of the reduced state of the dye, wherein the presence of (D)-2-hydroxyglutarate in the sample of the subject is indicative for a mutation in an isocitrate dehydrogenase (IDH) gene or in a (D)-2-hydroxyglutarate dehydrogenase gene in said subject.

14. The method of claim 13, wherein said mutation in an isocitrate dehydrogenase (IDH) gene is a mutation in the IDH1 gene or IDH2 gene.

15. A kit comprising (i) a solvent, (ii) a dye having an oxidized state and a reduced state, wherein the reduced state can be distinguished from the oxidized state and wherein the dye is initially present in the oxidized state, (iii) an electron transfer agent, a (D)-2-hydroxyglutarate dehydrogenase enzyme, and a cofactor.

* * * * *